(12) United States Patent
Ichim et al.

(10) Patent No.: US 11,504,410 B2
(45) Date of Patent: Nov. 22, 2022

(54) NEUROPROTECTION AND NEUROREGENERATION BY PTEROSTILBENE AND COMPOSITIONS THEREOF

(71) Applicant: THERAPEUTIC SOLUTIONS INTERNATIONAL, INC., Oceanside, CA (US)

(72) Inventors: Thomas E. Ichim, Oceanside, CA (US); Timothy G. Dixon, Oceanside, CA (US); James Veltmeyer, Oceanside, CA (US)

(73) Assignee: Therapeutic Solutions International, Inc., Oceanside, CA (US)

( * ) Notice: Subject to any disclaimer, the term of this patent is extended or adjusted under 35 U.S.C. 154(b) by 9 days.

(21) Appl. No.: 17/387,158

(22) Filed: Jul. 28, 2021

(65) Prior Publication Data
US 2022/0031793 A1 Feb. 3, 2022

Related U.S. Application Data

(60) Provisional application No. 63/057,315, filed on Jul. 28, 2020.

(51) Int. Cl.
*A61K 36/82* (2006.01)
*A61K 31/09* (2006.01)
*A61K 36/45* (2006.01)
*A61K 31/26* (2006.01)
*A61K 36/31* (2006.01)
*A61K 31/353* (2006.01)
*A61K 31/122* (2006.01)
*A61K 36/71* (2006.01)

(52) U.S. Cl.
CPC ........... *A61K 36/82* (2013.01); *A61K 31/09* (2013.01); *A61K 31/122* (2013.01); *A61K 31/26* (2013.01); *A61K 31/353* (2013.01); *A61K 36/31* (2013.01); *A61K 36/45* (2013.01); *A61K 36/71* (2013.01)

(58) Field of Classification Search
CPC .. A61K 2300/00; A61K 31/09; A61K 31/122; A61K 31/26; A61K 31/353; A61K 36/31; A61K 36/45; A61K 36/71; A61K 36/82
See application file for complete search history.

(56) References Cited

U.S. PATENT DOCUMENTS 11,266,707 B2 * 3/2022 Ichim .................... A61K 31/26

* cited by examiner

*Primary Examiner* — Aaron J Kosar
(74) *Attorney, Agent, or Firm* — Baumgartner Patent Law; Marc Baumgartner

(57) ABSTRACT

Disclosed are means, compositions of matter, and protocols useful for neuroprotection and neuroregeneration. In one embodiment the invention provides administration of pterostilbene alone or in combination with other ingredients to induce neuroprotection and/or neuroregeneration. The invention teaches protection/regeneration in conditions associated with neurological inflammation and/or other congenital or acquired neurodegenerative diseases.

19 Claims, 12 Drawing Sheets

NEUROPROTECTION AND NEUROREGENERATION BY PTEROSTILBENE AND COMPOSITIONS THEREOF

CROSS-REFERENCE TO RELATED APPLICATIONS

This application claims priority to U.S. Provisional Application No. 63/057,315, filed Jul. 28, 2021, which is incorporated herein by reference in its entirety.

FIELD OF THE INVENTION

The invention relates to the field of protecting and regenerating neurological tissue, more specifically, the administration of pterostilbene in combination with nutraceuticals to a subject in need.

BACKGROUND

Neurodegeneration refers to the progressive loss of structure or function of neurons, including death of neurons. This deterioration gradually causes a loss of cognitive abilities such as memory and decision making. Neurodegeneration is a key aspect of a large number of diseases encompassed under the term, "neurodegenerative diseases." Although hundreds of different neurodegenerative disorders exist, research and attention have primarily focused on amyotrophic lateral sclerosis ("ALS"), Parkinson disease ("PD") Huntington disease ("HD"), and Alzheimer disease ("AD"). All of these conditions lead to progressive brain damage and neurodegeneration. The causes of these neurodegenerative diseases are essentially unknown, and even when they have been identified, the mechanisms by which they initiate the disease remain speculative. At the present time, these neurodegenerative diseases are incurable.

Stroke is the third leading cause of death and disability in adults in the US. Unfortunately, thrombolytic therapy only benefits about 2% of the ischemic stroke patients. The dismal record of neurorestorative regimens for stroke both in the laboratory and the clinic demands an urgent need to develop novel therapies. Because the secondary cellular death that ensues after the initial stroke episode occurs over an extended time. Treatment strategies directed at rescuing these ischemic neurons have the potential to retard the disease progression and even afford restoration of function. The recognition of this delay in secondary stroke-induced pathophysiologic alterations has prompted investigations on neurorestorative treatments.

It is known that the ischemic type of stroke, caused by blockage of a brain artery accounts for 87% of the cases. Subsequent to the ischemic injury, which is associated with a interruption of glucose and oxygen supply to the brain—the area with severe hypoperfusion is known as the core of the infarct where neuronsare lethally injured. This area is variably surrounded by a less hypoperfused area (known as the penumbra) where cells are still metabolically active for a certain period and—depending on circumstances—will either die or survive [1].

Neuronal cell death in stroke is multifactorial and complex [2], comprising several components that contribute to excitotoxicity, oxidative stress, mitochondrial dysfunction, and neuroinflammation. To find mechanisms of neuroprotection for this area is an active focus of research. At present, however, the only therapeutic options are local recanalization and systemic thrombolysis, which have a short therapeutic window, with only 20% of patients eligible for these treatments [3].

As one would expect, the extent of permanent damage is proportional to the duration of the ischemic episode; therefore, to restore the blood flow as soon as possible is fundamental. Unfortunately, it is also known that the process of restoring circulation after ischemia causes the generation of reactive oxygen species (ROS) and nitrosylation, which in turn activates the immunological response, leading to neuroinflammation with detrimental consequences. During neuroinflammation, the first cells to react to the ischemic injury are microglia cells (i.e., the resident immune cells of the brain), and the immune response is followed by infiltration of macrophages, lymphocytes, neutrophils, and dendritic cells to the ischemic parenchyma due to blood-brain barrier breakdown, which exacerbates the damage. Neuroinflammation may also play an essential role in brain damage and brain repair.

Neurons, due to their inherent high demand of energy, are very sensitive to the lack of glucose and ATP and are the first brain cells to die in the area directly affected by the lack of blood flow [4, 5]. Loss of neurons can continue for hours or even days after reperfusion, depending on the cellular characteristics of the area affected.

Neuronal cell death is not an isolated process, implicating a full response from various brain cells. On the one hand, neurons are connected to each other forming an extensive communication network through synaptic transmission. Failure in the synaptic process causes disconnection and transsynaptic degeneration, leading to neuronal dysfunction and cell death to neurons that are in related cerebral structures. The term diaschisis is defined as a dysfunction in an area of the brain connected to a distant, damaged, brain area[1]. The primary mechanisms of diaschisis are functional and structural deafferentiation that lead to loss of input information from the damaged brain area. This is followed at later stages by reorganization of distributed brain networks in the distantly targeted area Diaschisis has mostly been described after focal stroke or traumatic brain injuries, however, recent evidence from neurodegenerative syndromes shows that trans-neuronal degeneration also occurs in Alzheimer's or Parkinson's diseases, suggesting that trans-synaptic dysfunction is an event common to a variety of brain pathologies. While functional deafferentiation is thought to be one of the primary mechanisms of diaschisis, the cellular and molecular mechanisms involved in trans-synaptic degeneration processes remain unknown. The control of glutamate release/recapture shapes normal brain functions, and alterations in glutamate neurotransmission are strongly associated with both acute and chronic degenerative processes. Indeed, glutamate, the most abundant excitatory neurotransmitter in the central nervous system, plays a key role in controlling neuronal activity-dependent survival pathways[7] that lead to the expression of pro-survival genes, increase of anti-oxidative defense factors, and inhibition of pro-apoptotic molecules. On the other hand, overstimulation of NMDA receptors (NMDAR) by excessive glutamate levels has long been associated with excitotoxicity-induced neuronal death through calcium increase, energetic imbalance, and activation of death associated pathways; possibly through extrasynaptic NMDAR activation. Glutamate therefore acts as a hub controlling neuronal network robustness under stress [6].

On the other hand, the field is starting to recognize important intimate interactions between all brain cells, such as the relationship between glial cells, neurons, and blood vessels in the so-called neurovascular unit (NVU). For example, the NVU regulates not only the cerebral blood flow according to the energy needs of the brain but also has a significant function in maintaining the blood-brain barrier. To maintain these structures, communication between cells is a key process.

The invention provides means of protecting brain cells against damage and in some situations inducing regeneration.

SUMMARY

The teaching herein relate to methods of protecting from damage and/or regenerating a neurological tissue comprising administration of pterostilbene, and/or Green Tea and/or extract thereof, and/or Blueberry and/or extract thereof; c) *Nigella Sativa* and/or extract thereof; and d) broccoli and/or extract thereof.

Preferred embodiments are directed to methods wherein said neurological protection is inhibition of neuronal apoptosis.

Preferred embodiments are directed to methods wherein said neurological protection is inhibition of neuronal dysfunction.

Preferred embodiments are directed to methods wherein said neurological protection is inhibition of neuronal excitotoxicity.

Preferred embodiments are directed to methods wherein said neurological protection is inhibition of neuronal oxidative stress.

Preferred embodiments are directed to methods wherein said neurological protection is upregulation of bcl-2.

Preferred embodiments are directed to methods wherein said neurological protection is downregulation of fas ligand.

Preferred embodiments are directed to methods wherein said neurological protection is downregulation of fas.

Preferred embodiments are directed to methods wherein said regeneration of said neurological tissue comprises stimulation of axonal re-connections.

Preferred embodiments are directed to methods wherein said regeneration of said neurological tissue comprises stimulation of proliferation of neural progenitor cells.

Preferred embodiments are directed to methods wherein said neural progenitor cells are endogenous.

Preferred embodiments are directed to methods wherein said neural progenitor cells are exogenous.

Preferred embodiments are directed to methods wherein said endogenous neural progenitor cells are originating from the subventricular zone.

Preferred embodiments are directed to methods wherein said endogenous neural progenitor cells are originating from the dentate gyrus of the hippocampus.

Preferred embodiments are directed to methods wherein said green tea extract is epigallocatechin-3-gallate or an analogue thereof.

Preferred embodiments are directed to methods wherein said blueberry extract is pterostilebene or an analogue thereof.

Preferred embodiments are directed to methods wherein said *Nigella Sativa* extract is thymoquinone or an analogue thereof.

Preferred embodiments are directed to methods wherein said broccoli extract is sulforaphane or an analogue thereof.

Preferred embodiments are directed to methods wherein said neurological damage is COVID-19 associated.

DETAILED DESCRIPTION OF THE INVENTION

Figure 1:
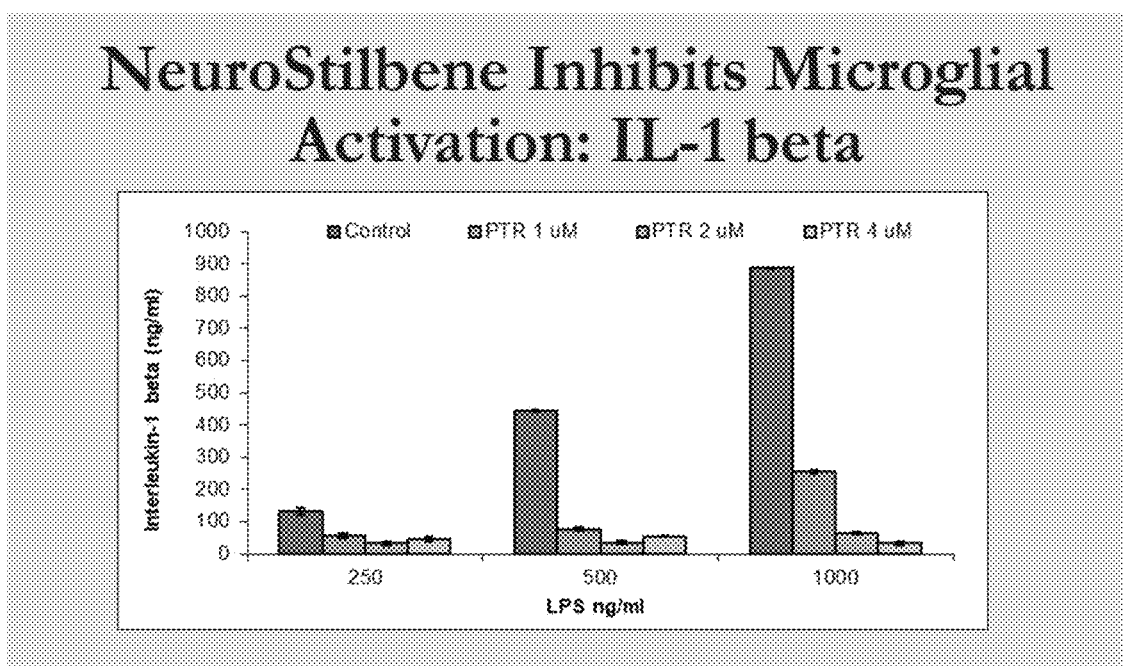
FIG. 1 is a bar graph showing NeuroStilbene inhibits microglial activation: IL-1 beta.

The invention provides the use of pterostilbene alone, in liposomal formulations, and in combination with other ingredients for stimulation of neurogenesis and/or induction of neuroprotection. It is known that neuroinflammatory conditions such as stroke are associated with induction of innate immunity. In one embodiment the invention teaches administration of pterostilbene and/or combinations containing pterostilbene for reduction of pathological innate inflammation.

Combination therapy: The term "combination therapy", as used herein, refers to those situations in which two or more different pharmaceutical agents are administered in overlapping regimens so that the subject is simultaneously exposed to both agents.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses.

Subject: As used herein, the term "subject" or "patient" refers to any organism upon which embodiments of the invention may be used or administered, e.g., for experimental, diagnostic, prophylactic, and/or therapeutic purposes.

Typical subjects include animals (e.g., mammals such as mice, rats, rabbits, non-human primates, and humans; insects; worms; etc.).

Suffering from: An individual who is "suffering from" a disease, disorder, or condition (e.g., stroke) has been diagnosed with and/or exhibits one or more symptoms of the disease, disorder, or condition.

Therapeutic regimen: As used herein, the term "therapeutic regimen" refers to any protocol used to partially or completely alleviate, ameliorate, relieve, inhibit, prevent, delay onset of, reduce severity of and/or reduce incidence of one or more symptoms or features of a particular disease, disorder, and/or condition. In some embodiments, a therapeutic regimen may comprise a treatment or series of treatments whose administration correlates with achievement of a particular result across a relevant population. In some embodiments, a therapeutic regimen involves administration of one or more therapeutic agents, either simultaneously, sequentially or at different times, for the same or different amounts of time. Alternatively, or additionally, the treatment may include exposure to protocols such as radiation, chemotherapeutic agents or surgery. Alternatively or additionally, a "treatment regimen" may include genetic methods such as gene therapy, gene ablation or other methods known to reduce expression of a particular gene or translation of a gene-derived mRNA.

Therapeutic agent: As used herein, the phrase "therapeutic agent" refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" refers to an amount of a therapeutic agent whose administration, when viewed in a relevant population, correlates with or is reasonably expected to correlate with achievement of a particular therapeutic effect. The therapeutic effect may be objective (i.e., measurable by some test or marker) or subjective (i.e., subject gives an indication of or feels an effect). A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" refers to a therapeutic protocol that alleviates, delays onset of, reduces severity or incidence of, and/or yield prophylaxis of one or more symptoms or aspects of a disease, disorder, or condition. In some embodiments, treatment is administered before, during, and/or after the onset of symptoms. In some embodiments, treatment may be administered to a subject who does not exhibit signs of a disease, disorder, and/or condition. In some embodiments, treatment may be administered to a subject who exhibits only early signs of the disease, disorder, and/or condition, for example for the purpose of decreasing risk of developing pathology associated with the disease, disorder, and/or condition.

As part of the inflammatory response to brain injury, numerous immunological cells become activated and participate in causation of pathology. One of the immediate reactions to the ischemia reperfusion injury is activation of the complement cascade. The complement system provides a first line of defense and mediates a large variety of cellular and humoral interactions in the immune response, including chemotaxis, phagocytosis, cell adhesion, B and T cell differentiation [7]. It consists of approximately 30 plasma proteins with an associated group of cell membrane proteins. Activation of complement by the classical, the alternative and the recently discovered lectin pathway generates opsonins, inflammatory mediators, and cytolytic protein complexes which play an essential role in clearing microorganisms and tissue damage products. There exist three complement pathways: the classical pathway, lectin pathway, and alternative pathway. This response involves soluble complement proteins, which make up approximately 5% of the total protein content of human blood plasma. In the classical pathway, the C1 complement protein is the initial responder of the classical pathway and is comprised of C1q, C1r, and C1s. In the presence of calcium, C1q, C1r, and C1s can form a complex that induces conformational changes in the collagen region of C1q to activate the classical pathway. Accordingly in some embodiments administration of pterostilbene is provided to reduce complement activation. The role of complement is described in detail below as relates to stroke but is relevant in other neurological deficiencies.

One of the early suggestions that complement may be involved in stroke came from a report in which researchers inhibited the classical complement activation pathway in a photochemical cortical vein occlusion model. Immediately after occlusion, rats were infused with either 0.9% saline (vehicle), or C1-esterase inhibitor (C1-INH) over 30 min. Regional cerebral blood flow (rCBF) decreased after occlusion, and was about 50% of baseline after 2 h. No difference was noted between experimental groups. Mean arterial blood pressure (MABP) and arterial blood gases were likewise unaffected by the treatment. However, administration of C1-INH had significantly reduced infarct volume by 72%, as evaluated after 5 days survival [8]. Similar protective results where obtained in another study in which ischemia was induced by intraluminal occlusion of the middle cerebral artery. After 2 hours, reperfusion was produced by removing the nylon monofilament occluding the artery. The effect of 15 U C1-INH (intravenously) was evaluated in terms of general and focal neurologic deficits, ischemic volume, neutral red staining (to identify the brain areas subject to ischemic damage), and glial fibrillary acidic protein immunoreactivity (to show astrocytic response). Forty-eight hours after ischemia, C1-INH significantly improved general and focal deficits by 36% and 54%, respectively, and significantly reduced infarct volume (C1-INH, 6.69%+/−2.93%; saline, 24.24%+/−8.24%) of total brain. Neutral red staining further showed the strong protective effect of C1-INH in cortex, hippocampus, and striatum [9]. Other studies performing complement depletion/inactivation, have shown successful reduction in stroke pathology [10-23].

The role of complement in brain ischemia situations may be attributed to locally produced complement factors. In one study, significant increases in the expression of C3aR and C5aR mRNAs in the ischemic cortex were observed; the expression of both reached a peak at 2 days after MCA occlusion. C3aR and C5aR stainings were found constitutively on neurons and astrocytes. In ischemic tissues, they observed that C3aR and C5aR were expressed de novo on endothelial cells of blood vessels, at 6 h and 2 days after MCA occlusion, respectively. C3aR and C5aR immunostaining was increased in macrophage-like cells and reactive astrocytes 7 days postocclusion [24]. The generation of complement proteins associated with ischemic insult to the brain was also found in experimentally induced global ischemia when the biosynthesis of C1q, the recognition subcomponent of the classical complement activation pathway, was examined in the CNS. Using semiquantitative in situ hybridization, immunohistochemistry, and confocal laser scanning microscopy, a dramatic and widespread increase of C1q biosynthesis in rat brain microglia (but not in astrocytes or neurons) within 24 h after the ischemic insult was observed. A marked increase of C1q functional activity in cerebrospinal fluid taken 1, 24, and 72 h after the ischemic insult was determined by C1q-dependent hemolytic assay. In the light of the well-established role of complement and complement activation products in the initiation and maintenance of inflammation, the ischemia-induced increase of cerebral C1q biosynthesis and of C1q functional activity in the cerebrospinal fluid implies that the proinflammatory activities of locally produced complement are likely to contribute to the pathophysiology of cerebral ischemia [25].

Without being bound by any particular theory, due to its improved solubility, pterostilbene is also expected to have better oral absorption properties compared to various other neuroprotectants. As used herein, "bioavailability" refers to the rate and amount of a drug or supplement that reaches the systemic circulation of a patient following administration of the drug or supplement. It has been found that the relative bioavailability of pterostilbene is at least about 50 percent greater than, for example, creatine monohydrate. The inventors of the present invention surprisingly discovered that compositions including pterostilbene provide an effective treatment for the prevention and reduction of neurodegeneration. The terms "treatment," "treating," and "treat, are used herein to refer generally to obtaining a desired pharmacological and/or physiological effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

the inflammation associated with stroke appears to be one of the main factors in creation of pathology. Complement activation is one of the main initial responses to the ischemic/reperfusion injury. Other responses include the major inflammatory reaction characterized by peripheral leukocyte influx into the cerebral parenchyma and the activation of endogenous microglia follows focal cerebral ischemia [26]. The microglia represent the third major population of glial cells within the central nervous system after astrocytes and oligodendrocytes. Microglia are distributed ubiquitously throughout the brain and spinal cord, and one of their main functions is to monitor and sustain neuronal health. Microglial cells are quite sensitive to even minor disturbances in CNS homeostasis, and they become readily activated during most neuropathologic conditions, including peripheral nerve injury, trauma and stroke, inflammatory disease, and neurotoxicant-induced neuronal injury. During activation, microglia display conspicuous functional plasticity, which involves changes in cell morphology, cell number, cell surface receptor expression, and production of growth factors and cytokines. The many changes occurring in activated cells reflect the altered functional states of microglia that are induced by signals arising from injured neurons [27]. One of the objects of the invention is to reduce microglial activation by administration of pterostilbene and/or combinations containing pterostilbene.

It is believed that the microglial activation occurs in part because of cessation of cerebral blood flow, which leads to energy depletion and necrotic neuron death, which can trigger immune responses ultimately leading to microglial response [28]. Reperfusion of the occluded vessel, either due to compensation by the collateral circulation, or spontaneous or therapeutic recanalization leads to the generation of reactive oxygen species(ROS) either by reperfusion with oxygenated blood or production within brain and immune cells. ROS canthen stimulate ischemic cells, even ischemic neurons, to secrete inflammatory cytokines and chemokines that cause, among other things, adhesion molecule upregulation in the cerebral vasculature and peripheral leukocyte recruitment, respectively [29, 30].

Activated microglia produce several mediators which cause damage to brain tissue. One well known pathological pathway is production of TNF-alpha. Using a middle cerebral artery ligation model, At 12 hours, a peak of 19.2+/−5.1 TNF mRNA-expressing cells/mm2 was counted, contrasting two to three times lower values at 6 and 24 hours (6.4+/−4.6 and 9.2+/−3.4 cells/mm2, respectively) and <2 cells/mm2 at 48 hours and later stages. The TNF mRNA-expressing cells were distributed along the entire rostrocaudal axis of the cortical infarcts and occasionally within the caudate putamen. At all time points, TNF mRNA colocalized with Mac-1-positive microglia/macrophages but not with Ly-6G (Gr-1)-positive polymorphonuclear leukocytes. Similarly, combined in situ hybridization for TNF mRNA and immunohistochemistry for glial fibrillary acidic protein at 12 and 24 hours revealed no TNF mRNA-expressing astrocytes at these time points. Translation of TNF mRNA into bioactive protein was demonstrated in the neocortex of C57Bl/6 mice subjected to permanent middle cerebral artery occlusion. These data point to a time-restricted microglial/macrophage production of TNF in focal cerebral ischemia in mice [31]. TNF-alpha at high concentrations is known to induce killing of neurons, as well as activation of various inflammatory pathways [32-34]. In some embodiments suppression of neuronal death is achieved by administration of pterostilbene and/or compounds containing pterostilbene.

Supporting a pathological role of TNF-alpha in stroke are studies that show suppression of TNF-alpha results in improved outcomes [35-40].

Therapies that inhibit microglial activation have been shown to possess some efficacy in decreasing stroke pathology. One example of reducing stroke damage, disclosed in the current invention is the combination of pterostilbene, together with inhibitors of microglia activation such as doxycycline and minocycline, which are broad-spectrum antibiotics and have antiinflammatory effects independent of their antimicrobial activity have been shown to inhibit microglial activation. Minocycline increased the survival of CA1 pyramidal neurons from 10.5% to 77% when the treatment was started 12 h before ischemia and to 71% when the treatment was started 30 min after ischemia. The survival with corresponding pre- and posttreatment with doxycycline was 57% and 47%, respectively. Minocycline prevented completely the ischemia-induced activation of microglia and the appearance of NADPH-diaphorase reactive cells, but did not affect induction of glial acidic fibrillary protein, a marker of astrogliosis. Minocycline treatment for 4 days resulted in a 70% reduction in mRNA induction of interleukin-1beta-converting enzyme, a caspase that is induced in microglia after ischemia. Likewise, expression of inducible nitric oxide synthase mRNA was attenuated by 30% in minocycline-treated animals [41]. In another study, Stroke was induced by photothrombosis in the forelimb sensorimotor cortex of Sprague-Dawley rats. Minocycline was administered for 2 days after stroke induction and the effects on forelimb function assessed up to 28 days. The responses of peri-infarct Iba1-positive cells and astrocytes were evaluated using immunohistochemistry and Western blots. Initial characterization showed that the numbers of Iba1-positive microglia and macrophages decreased in peri-infarct tissue at 24 h then increased markedly over the next few days. Morphological changes characteristic of activation were readily apparent by 3 h and increased by 24 h. Minocycline treatment improved the rate of recovery of motor function as measured by a forelimb placing test but did not alter infarct volume. At 3 days, there were only minor effects on core features of peri-infarct microglial reactivity including the morphological changes and increased density of Iba1-positive cells. The treatment caused a decrease of 57% in the small subpopulation of cells that expressed CD68, a marker of phagocytosis [42]. Other agents that inhibit microglial activation that can be used together with the current invention include Fasudil [43], apelin-13 [44], atorvastatin [45], hyperbaric oxygen [46], paeonol [47], melatonin [48], histone deacetylase inhibitors [49, 50], caffeic acid phenethyl ester [51, 52], interleukin-10 [53], pyruvate [54], bone marrow mononuclear cells [55, 56], bone marrow mesenchymal stem cells [57], PD-1 [58], compound K [20-O-D-glucopyranosyl-20(S)-protopanaxadiol] [59], Glycyrrhizic acid [60].

In some embodiments pterostilbene and combinations involving pterostilbene are administered to induce immune modulation of T cells to prevent neurodegeneration. One suggestive study supporting the notion that T cells are involved in stroke pathology is situations in which inhibitors of T cell activation are administered and protect against ischemia induced brain injury. In one study both common carotid arteries were ligated bilaterally in 40 male Wistar rats. Twenty-two of these rats received an intraperitoneal injection of cyclosporin A, and the remaining 18 received a vehicle-solution injection. Microglia/macrophages were investigated with immunohistochemistry for the major histocompatibility complex class I and II antigens as well as for leukocyte common antigen. Astroglia were examined with glial fibrillary acidic protein as a marker. Activation of glial cells and white matter rarefaction were then investigated from 7 to 30 days after the ligation. In vehicle-treated animals, there was a persistent and extensive activation of both microglia/macrophages and astroglia in the white matter, including the optic nerve, optic tract, corpus callosum, internal capsule, and traversing fiber bundles of the caudoputamen. In cyclosporin A-treated rats, the number of activated microglia/macrophages was significantly reduced (P<0.01) to approximately one fifth of that in vehicle-treated animals. Similarly, rarefaction of the white matter was much less intense in cyclosporin A-treated rats (P<0.01). Cyclosporin A suppressed both glial activation and white matter changes after chronic cerebral hypoperfusion [61]. Another suggestion that the adaptive immune system may be involved in stroke are findings that splenectomy, which is known to be immune modulatory, is associated with better outcome in stroke. In one study, rats were splenectomized 2 weeks before permanent middle cerebral artery occlusion had a >80% decrease in infarction volume in the brain compared with those rats that were subjected to the stroke surgery alone. Splenectomy also resulted in decreased numbers of activated microglia, macrophages, and neutrophils present in the brain tissue. These results demonstrate that the peripheral immune response as mediated by the spleen is a major contributor to the inflammation that enhances neurodegeneration after stroke [62].

Scientists have previously reported that increased microvessel density in the peri-infarct area correlates with longer survival times in ischemic stroke patients [63-65]. This raises the possibility that enhancement of angiogenesis is one of the strategies to facilitate functional recovery after ischemic stroke [66-69]. Intriguingly, blood vessels and axons are tightly joined and run parallel throughout the central nervous system, suggesting a coupling of both components. It is known that situations such as stroke, cause ischemia, and ischemia stimulate production of new blood vessels through multiple mechanisms. Some mechanisms include stimulation of hypoxia inducible factor (HIF)-1 activation and its nuclear translocation [70-75]. This causes generation of transcription of numerous genes including angiogenic genes such as SDF-1 [76-80], which attract endothelial progenitor cells, genes such as VEGF [81, 82], which trigger formation of new blood vessels, and genes such as PD-L1 which suppress inflammation in an attempt to restore new tissue growth and not fibrosis. Other means of HIF-1 alpha beneficial activity in stroke include activation of endogenous stem cells/repair of endothelium inside the brain of the stroke victim [83-86]. Other mechanisms of protection from stroke damage by HIF-1 alpha include protection of astrocytes from glutamate toxicity [87].

In other embodiments, pterostilbene and compounds associated with pterostilbene are administered to induce angiogenesis. Post-ischemic angiogenesis may modulate 1) axonal outgrowth and 2) neurogenesis, including proliferation, migration, and maturation of neural stem/progenitor cells (NSCs), and it is thought to contribute to functional recovery. Following ischemic stroke, administration of bone marrow cells may be correlated with improved regional cerebral blood flow, regional metabolic rate of oxygen consumption, and improved neurological function [88-139]. Therapeutic effects in stroke of other pro-angiogenic growth factors have also been described. For example, an FGF2 apatite coating was developed as a slow-releasing drug delivery system (DDS) by forming an FGF2/calcium phosphate composite layer. Hydroxyapatite was coated with high or low doses of FGF2, denoted as FGF-high and FGF-low. This study investigated the efficacy of the coating as angiogenesis therapy for brain infarction. Rats were subjected to permanent occlusion of the middle cerebral artery, an FGF2 apatite-coated implant was inserted, and the rat brains were removed 2 weeks after implantation. Rats in groups treated with FGF-high had significantly smaller areas of brain infarction, particularly in the external capsule and the lateral side of the putamen, and better capillary density than rats in groups treated with non-FGF2 apatite-coated implants. Histologic analysis indicated that the new vessels were larger and had thicker walls in the FGF2 apatite-coated groups than in the non-FGF2 groups. Fluorescence immunohistochemistry of the peri-infarction region showed that FGF2 released from FGF2 apatite-coated implants might have biological activity. Moreover, fluorescence immunohistochemistry showed that released FGF2 influenced microglia cells [140].

In one interesting experiment, permanent middle cerebral artery occlusion was performed in mice whose bone marrow (BM) had been replaced with BM cells from green fluorescent protein (GFP)-transgenic mice. The occluded mice were treated with G-CSF and SCF in the acute phase (days 1 to 10) or subacute phase (days 11 to 20), and the brain functions and histological changes were evaluated. Separately, the researchers injected bromodeoxyuridine during cytokine treatment to assess cell kinetics in the brain. Six mice were prepared for each experimental group. Administration of G-CSF and SCF in the subacute phase effectively improved not only motor performance but also higher brain function, compared with acute-phase treatment. Acute-phase and subacute-phase treatments identically reduced the infarct volume relative to vehicle treatment. However, subacute-phase treatment significantly induced transition of BM-derived neuronal cells into the peri-infarct area and stimulated proliferation of intrinsic neural stem/progenitor cells in the neuroproliferative zone. It was concluded that administration of G-CSF and SCF in the subacute phase after focal cerebral ischemia is effective for functional recovery, enhancing cytokine-induced generation of neuronal cells from both BM-derived cells and intrinsic neural stem/progenitor cells [141]. In another study, BM cells were harvested from green fluorescent protein-transgenic mice and were cultured. The mice were subjected to permanent middle cerebral artery occlusion. The BM or vehicle was transplanted into the ipsilateral striatum 7 d after the insult. Using autoradiography and fluorescence immunohistochemistry, we evaluated the binding of 125I-iomazenil and the expression of GABA receptor protein in and around the cerebral infarct 4 wk after transplantation. It was found that binding of 125I-iomazenil was significantly higher in the periinfarct neocortex in the BMSC-transplanted animals than in the vehicle-transplanted animals. Likewise, the number of the GABAA receptor-positive cells was significantly higher in the periinfarct neocortex in the BMSC-transplanted animals than in the vehicle-transplanted animals. A certain subpopulation of the transplanted BMSC expressed a neuron-specific marker, microtubule-associated protein 2, and the marker protein specific for GABAA receptor in the periinfarct area. These findings suggest that BMSC may contribute to neural tissue regeneration through migrating toward the periinfarct area and acquiring the neuron-specific receptor function [142].

In another embodiment, administration of pterostilbene is performed in order to enhance proliferation of endogenous neural progenitor cells. It does appear that in some studies administered stem cells stimulate proliferation of endogenous neural progenitors, or at least contribute to protection of these cells, in part through stimulation of angiogenesis. For example, in one study, bone marrow-derived MSCs were transplanted into the brain parenchyma 3 days after induction of stroke by occluding middle cerebral artery for 2 h. Stoke induced proliferation of resident neural stem cells in subventricular zone. However, most of new born cells underwent cell death and had a limited impact on functional recovery after stroke. Transplantation of MSCs enhanced proliferation of endogenous neural stem cells while suppressing the cell death of newly generated cells. Thereby, newborn cells migrated toward ischemic territory and differentiated in ischemic boundaries into double cortin+neuroblasts at higher rates in animals with MSCs compared to control group. The study indicates that therapeutic effects of MSCs are at least partly ascribed to dual functions of MSCs by enhancing endogenous neurogenesis and protecting newborn cells from deleterious environment [143]. There may be interaction between injected stem cells and the microglia, in which said microglia may act as a key factor in stimulation of proliferation of endogenous neural stem cells. For example, in one study observations where reported of increased numbers of activated microglia in ipsilateral SVZ concomitant with neuroblast migration into the striatum at 2, 6, and 16 weeks, with maximum at 6 weeks, following 2 h middle cerebral artery occlusion in rats. In the peri-infarct striatum, numbers of activated microglia peaked already at 2 weeks and declined thereafter. Microglia in SVZ were resident or originated from bone marrow, with maximum proliferation during the first 2 weeks post insult. In SVZ, microglia exhibited ramified or intermediate morphology, signifying a downregulated inflammatory profile, whereas amoeboid or round phagocytic microglia were frequent in the peri-infarct striatum. Numbers of microglia expressing markers of antigen-presenting cells (MHC-II, CD86) increased in SVZ but very few lymphocytes were detected. Using quantitative PCR, strong short- and long-term increase (at 1 and 6 weeks postinfarct) of insulin-like growth factor-1 (IGF-1) gene expression was detected in SVZ tissue. Elevated numbers of IGF-1-expressing microglia were found in SVZ at 2, 6, and 16 weeks after stroke. At 16 weeks, 5% of microglia but no other cells in SVZ expressed the IGF-1 protein, which mitigates apoptosis and promotes proliferation and differentiation of NSCs. The long-term accumulation of microglia with proneurogenic phenotype in the SVZ implies a supportive role of these cells for the continuous neurogenesis after stroke [144].

In other embodiments pterostilbene, and/or green tea extract and/or nigella *sativa* extract, and/or broccoli extract are administered together with agents selected from the following for stimulation of neuroprotection/neuroregeration: vascular endothelial growth factor (VEGF) [145-163], transforming growth factor-β [164], angiopoetin-1 [165, 166], platelet-derived growth factor-B [167-173], BDNF [57, 174-177], GDF-11 [178, 179], and progranulin [180].

Figure 2:
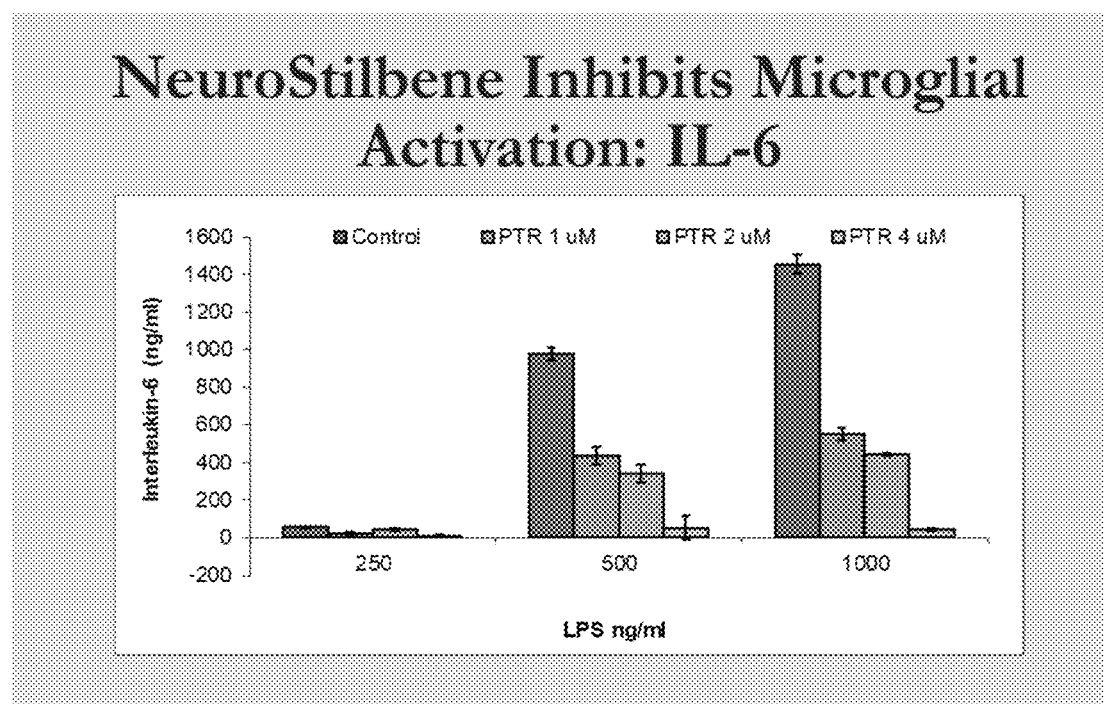
FIG. 2 is a bar graph showing NeuroStilbene inhibits microglial activation: IL-6 beta.
Figure 3:
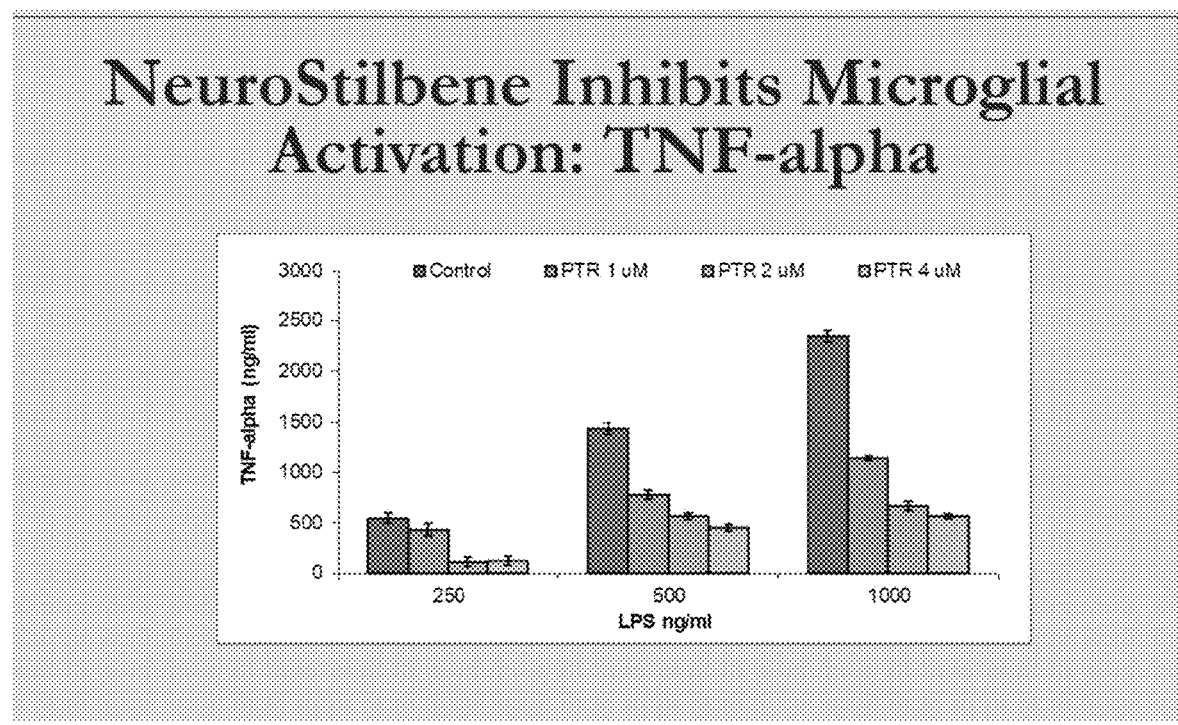
FIG. 3 is a bar graph showing NeuroStilbene inhibits microglial activation: TNF-alpha.
Figure 4:
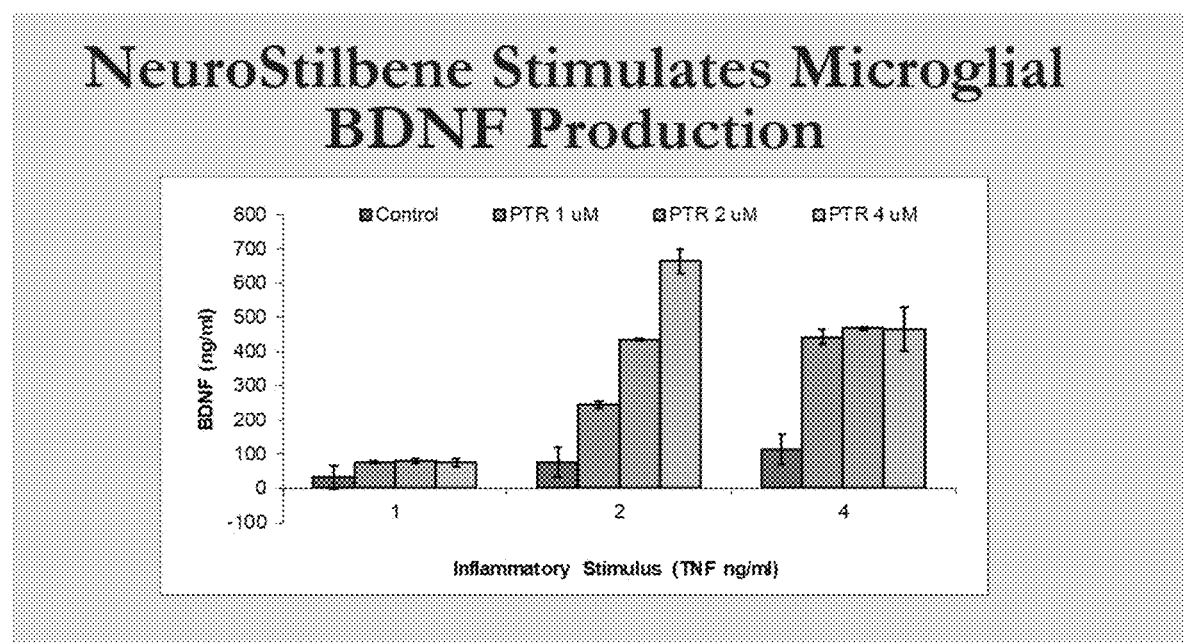
FIG. 4 is a bar graph showing NeuroStilbene stimulates microglial BDNF production.
Figure 5:
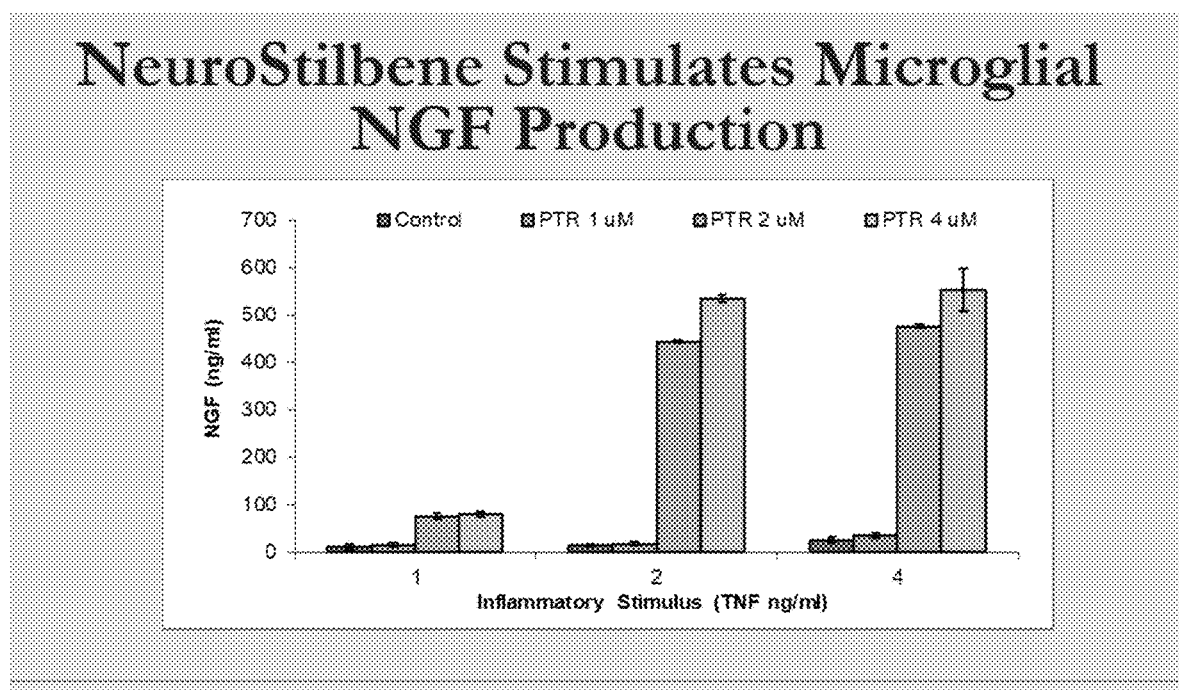
FIG. 5 is a bar graph showing NeuroStilbene stimulates microglial NGF production.
Figure 6:
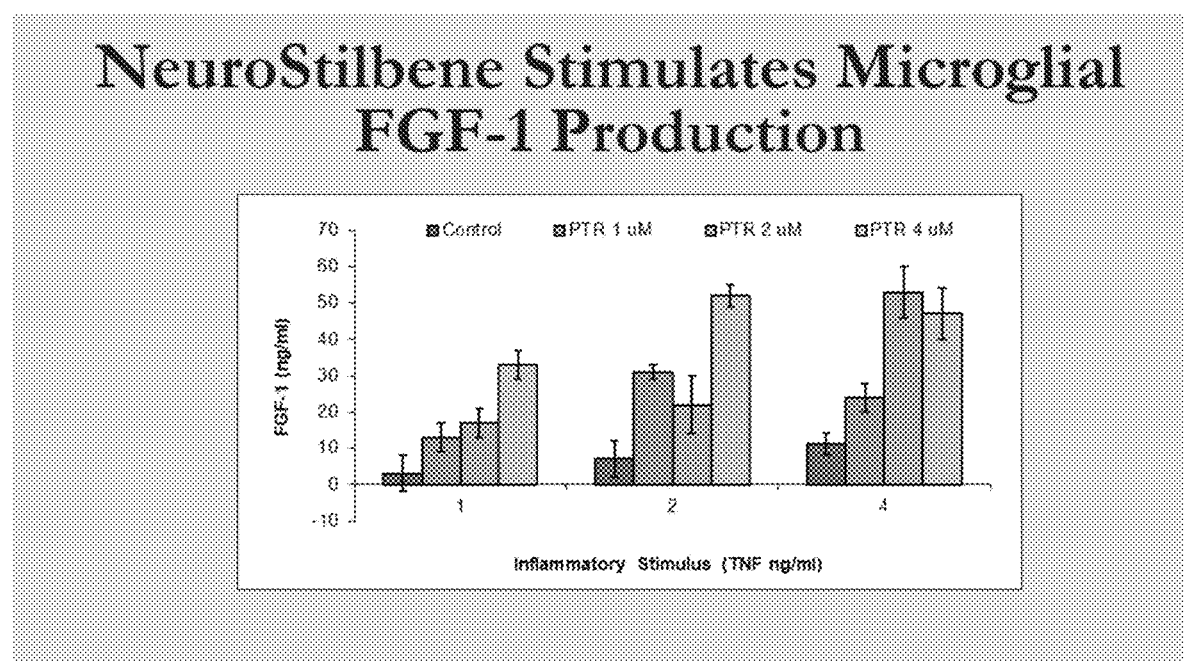
FIG. 6 is a bar graph showing NeuroStilbene stimulates microglial FGF-1 production.
Figure 7:
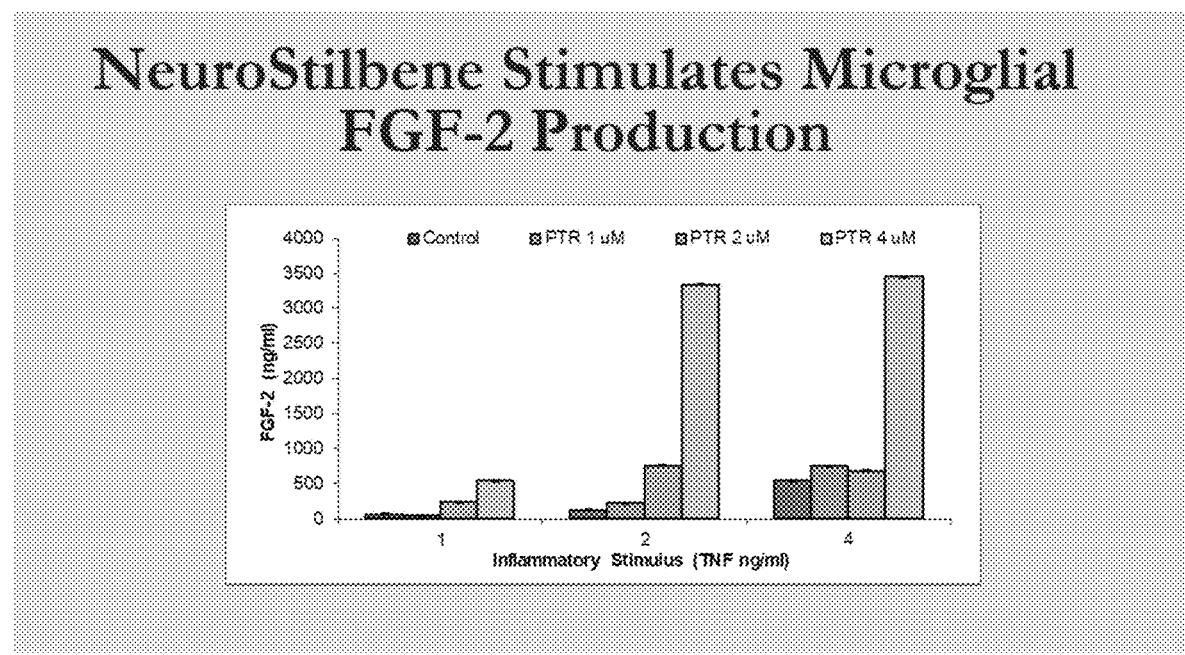
FIG. 7 is a bar graph showing NeuroStilbene stimulates microglial FGF-2 production.
Figure 8:
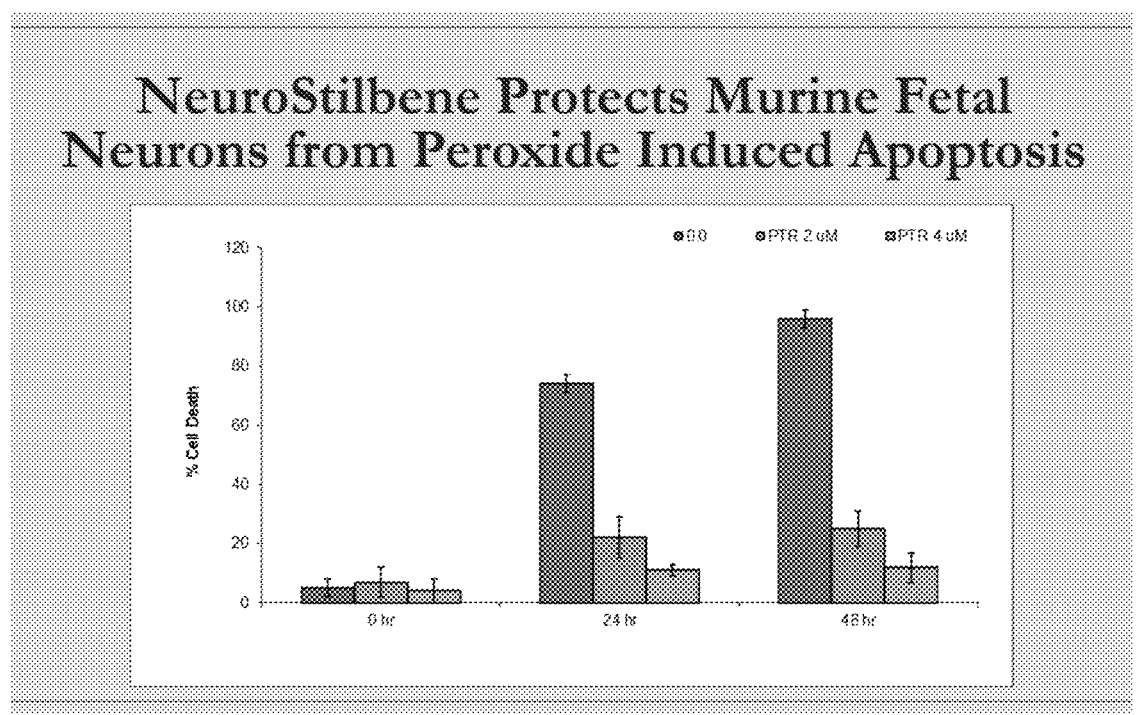
FIG. 8 is a bar graph showing NeuroStilbene protects murine fetal neurons from peroxide induced apoptosis.
Figure 9:
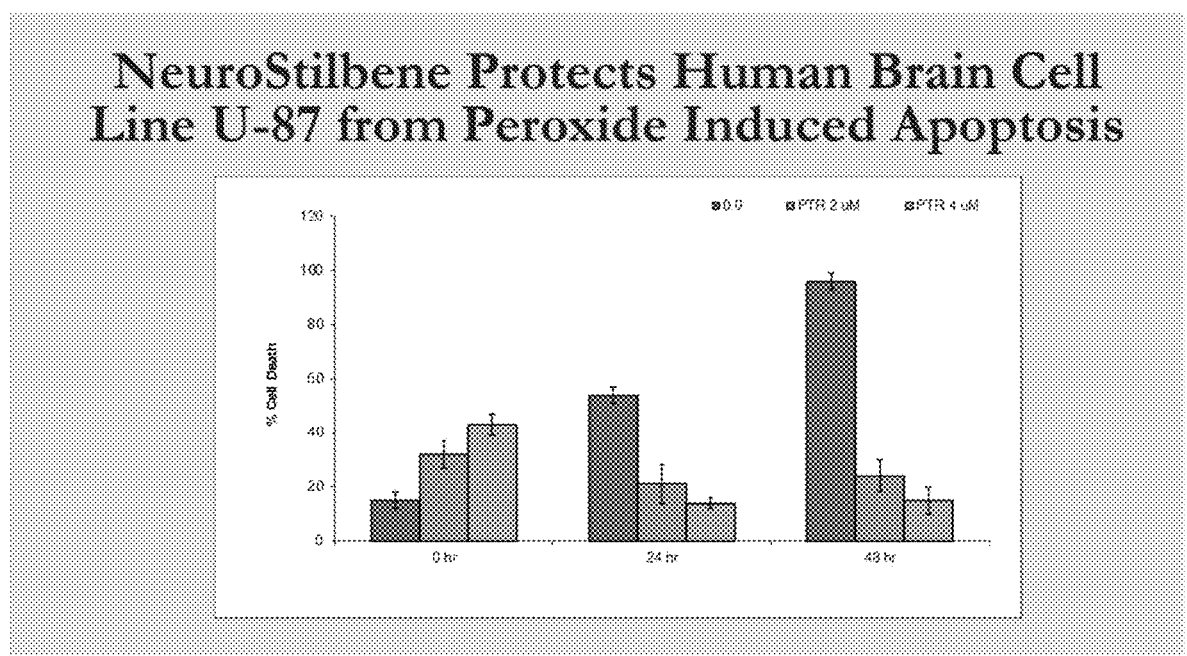
FIG. 9 is a bar graph showing NeuroStilbene protects human brain cell line U-87 from peroxide induced apoptosis.
Figure 10:
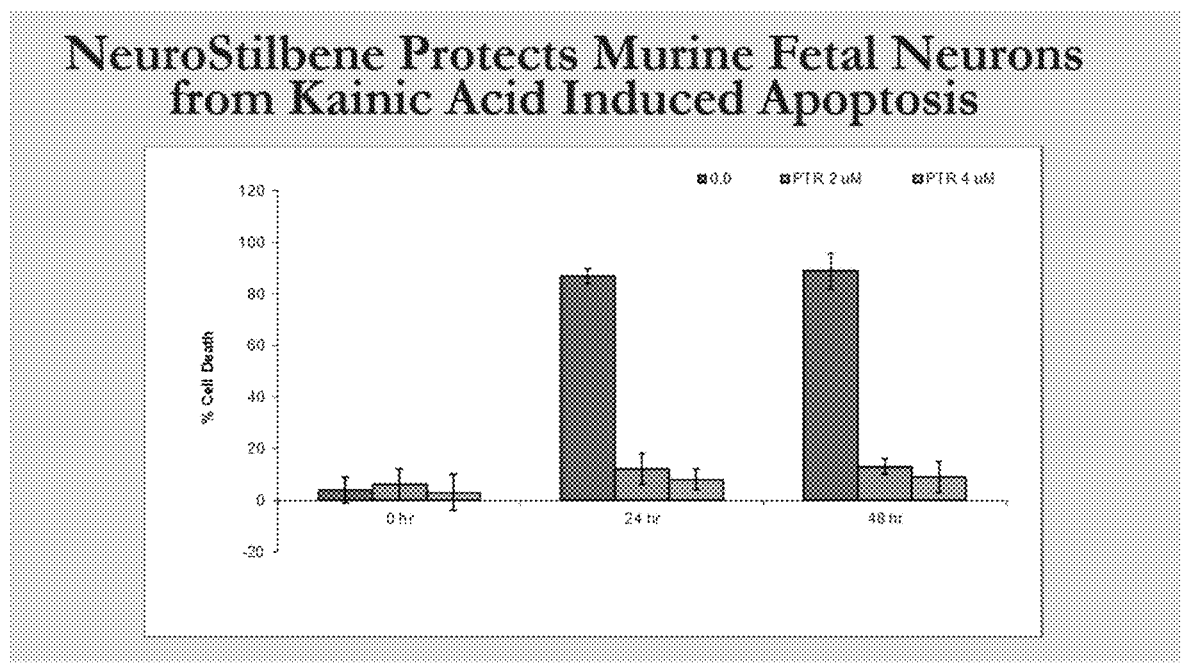
FIG. 10 is a bar graph showing NeuroStilbene protects murine fetal neurons from Kainic Acid induced apoptosis.
Figure 11:
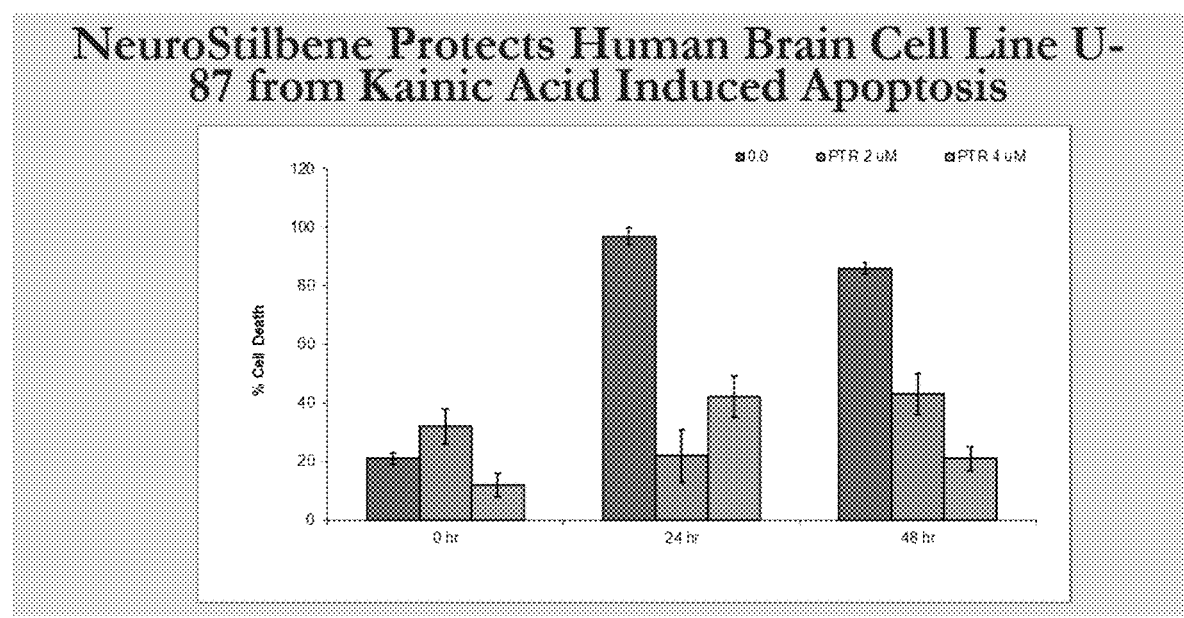
FIG. 11 is a bar graph showing NeuroStilbene protects human brain cell line U-87 from Kainic Acid induced apoptosis.
Figure 12:
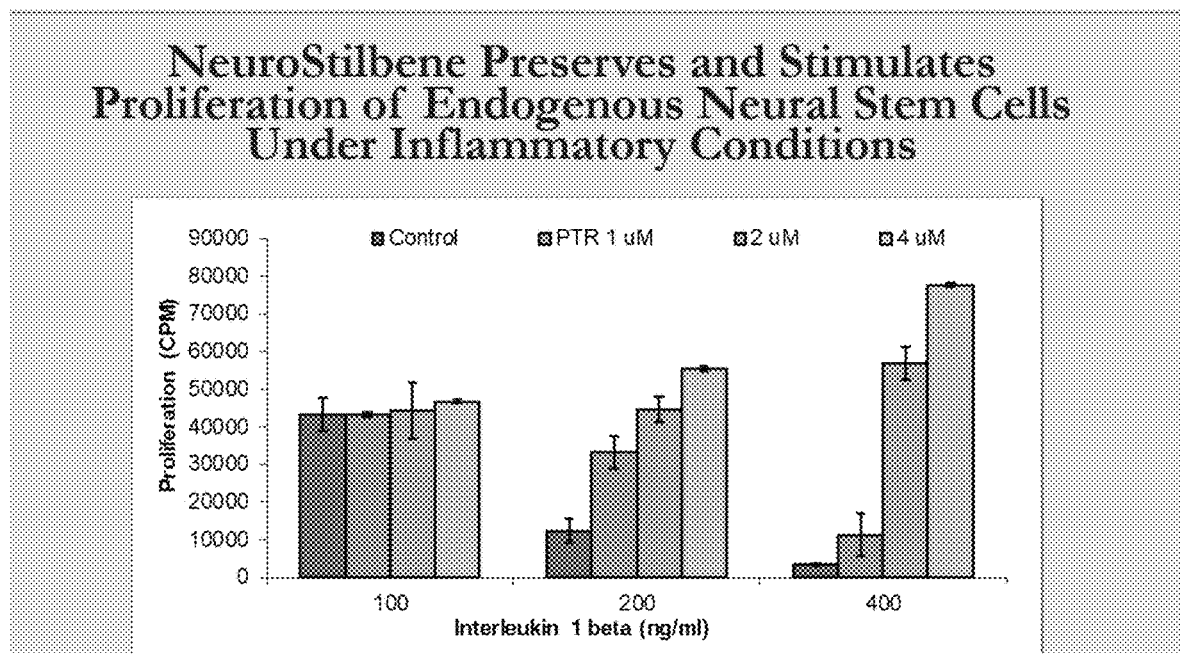
FIG. 12 is a bar graph showing NeuroStilbene preserves and stimulates proliferation of endogenous neural stem cells under inflammatory conditions.

Multiple experiments using NeuroStilbene were conducted to show their efficacy in protecting and regenerating neurological tissues. The results are shown in FIGS. 1-12.

CL REFERENCES

1. Waqas M, Rai A T, Vakharia K, Chin F, Siddiqui A H: Effect of definition and methods onestimates of prevalence of large vessel occlusion in acute ischemic stroke: a systematic review and meta-analysis. *J Neurointerv Surg* 2019.
2. Uzdensky A B: Apoptosis regulation in the penumbra after ischemic stroke: expression of pro- and antiapoptotic proteins. *Apoptosis* 2019, 24(9-10):687-702.
3. Smith W S: Endovascular Stroke Therapy. *Neurotherapeutics* 2019, 16(2):360-368.
4. D'Orsi B, Bonner H, Tuffy L P, Dussmann H, Woods I, Courtney M J, Ward M W, Prehn J H: Calpains are downstream effectors of bax-dependent excitotoxic apoptosis. *J Neurosci* 2012, 32(5):1847-1858.
5. Caldeira M V, Curcio M, Leal G, Salazar I L, Mele M, Santos A R, *Melo* C V, Pereira P, Canzoniero L M, Duarte C B: Excitotoxic stimulation downregulates the ubiquitin-proteasomesystem through activation of NMDA receptors in cultured hippocampal neurons. *Biochim Biophys Acta* 2013, 1832(1):263-274.
6. Deleglise B, Lassus B, Soubeyre V, Doulazmi M, Brugg B, Vanhoutte P, Peyrin J M: Dysregulated Neurotransmission induces Trans-synaptic degeneration in reconstructed Neuronal Networks. *Sci Rep* 2018, 8(1):11596.
7. Cho K: Emerging Roles of Complement Protein C1q in Neurodegeneration. *Aging Dis* 2019, 10(3):652-663.
8. Heimann A, Takeshima T, Horstick G, Kempski O: C1-esterase inhibitor reduces infarct volume after cortical vein occlusion. *Brain Res* 1999, 838(1-2):210-213.
9. De Simoni M G, Storini C, Barba M, Catapano L, Arabia A M, Rossi E, Bergamaschini L: Neuroprotection by complement (C1) inhibitor in mouse transient brain ischemia. *J Cereb Blood Flow Metab* 2003, 23(2):232-239.
10. Figueroa E, Gordon L E, Feldhoff P W, Lassiter H A: The administration of cobra venom factor reduces post-ischemic cerebral injury in adult and neonatal rats. *Neurosci Lett* 2005, 380(1-2):48-53.
11. Ten V S, Sosunov S A, Mazer S P, Stark R I, Caspersen C, Sughrue M E, Botto M, Connolly E S, Jr., Pinsky D J: C1q-deficiency is neuroprotective against hypoxic-ischemic brain injury in neonatal mice. *Stroke* 2005, 36(10): 2244-2250.
12. Mocco J, Mack W J, Ducruet A F, Sosunov S A, Sughrue M E, Hassid B G, Nair M N, Laufer I, Komotar R J, Claire M et al: Complement component C3 mediates inflammatory injury following focal cerebral ischemia. *Circ Res* 2006, 99(2):209-217.
13. Mocco J, Mack W J, Ducruet A F, King R G, Sughrue M E, Coon A L, Sosunov S A, Sciacca R R, Zhang Y, Marsh H C, Jr. et al: Preclinical evaluation of the neuroprotective effect of soluble complement receptor type 1 in a nonhuman primate model of reperfused stroke. JNeurosurg 2006, 105(4):595-601.
14. Arumugam T V, Tang S C, Lathia J D, Cheng A, Mughal M R, Chigurupati S, Magnus T, Chan S L, Jo D G, Ouyang X et al: Intravenous immunoglobulin (IVIG) protects the brain against experimental stroke by preventing complement-mediated neuronal cell death. *Proc Natl Acad Sci USA* 2007, 104(35):14104-14109.
15. Arumugam T V, Woodruff T M, Lathia J D, Selvaraj P K, Mattson M P, Taylor S M: Neuroprotection in stroke by complement inhibition and immunoglobulin therapy. *Neuroscience* 2009, 158(3):1074-1089.
16. Kim G H, Mocco J, Hahn D K, Kellner C P, Komotar R J, Ducruet A F, Mack W J, Connolly E S, Jr.: Protective effect of C5a receptor inhibition after murine reperfused stroke. *Neurosurgery* 2008, 63(1):122-125; discussion 125-126.
17. Pedersen E D, Loberg E M, Vege E, Daha M R, Maehlen J, Mollnes T E: In situ deposition of complement in human acute brain ischaemia. *Scand J Immunol* 2009, 69(6):555-562.
18. Heydenreich N, Nolte M W, Gob E, Langhauser F, Hofmeister M, Kraft P, Albert-Weissenberger C, Brede M, Varallyay C, Gobel K et al: C1-inhibitor protects from brain ischemia-reperfusion injury by combined antiinflammatory and antithrombotic mechanisms. Stroke 2012, 43(9):2457-2467.
19. Ducruet A F, Zacharia B E, Sosunov S A, Gigante P R, Yeh M L, Gorski J W, Otten M L, Hwang R Y, DeRosa P A, Hickman Z L et al: Complement inhibition promotes endogenous neurogenesis and sustained anti-inflammatory neuroprotection following reperfused stroke. *PLoS One* 2012, 7(6):e38664.
20. Yang J, Ahn H N, Chang M, Narasimhan P, Chan P H, Song Y S: Complement component 3 inhibition by an antioxidant is neuroprotective after cerebral ischemia and reperfusion inmice. *J Neurochem* 2013, 124(4):523-535.
21. Alawieh A, Elvington A, Zhu H, Yu J, Kindy M S, Atkinson C, Tomlinson S: Modulation of post-stroke degenerative and regenerative processes and subacute protection by site-targeted inhibition of the alternative pathway of complement. *J Neuroinflammation* 2015,12: 247.
22. Lai W, Xie X, Zhang X, Wang Y, Chu K, Brown J, Chen L, Hong G: Inhibition of Complement Drives Increase in Early Growth Response Proteins and Neuroprotection Mediated by Salidroside After Cerebral Ischemia. *Inflammation* 2018, 41(2):449-463.
23. Alawieh A, Andersen M, Adkins D L, Tomlinson S: Acute Complement Inhibition Potentiates Neurorehabilitation and Enhances tPA-Mediated Neuroprotection. *J Neurosci* 2018, 38(29):6527-6545.
24. Van Beek J, Bernaudin M, Petit E, Gasque P, Nouvelot A, MacKenzie E T, Fontaine M: Expression of receptors for complement anaphylatoxins C3a and C5a following permanentfocal cerebral ischemia in the mouse. *Exp Neurol* 2000, 161(1):373-382.
25. Schafer M K, Schwaeble W J, Post C, Salvati P, Calabresi M, Sim R B, Petry F, Loos M, Weihe E: Complement C1q is dramatically up-regulated in brain microglia in response to transient global cerebral ischemia. *J Immunol* 2000, 164(10):5446-5452.
26. Morioka T, Kalehua A N, Streit W J: Characterization of microglial reaction after middle cerebral artery occlusion in rat brain. *J Comp Neurol* 1993, 327(1):123-132.
27. Streit W J: Microglial response to brain injury: a brief synopsis. *Toxicol Pathol* 2000, 28(1):28-30.
28. Kato H, Tanaka S, Oikawa T, Koike T, Takahashi A, Itoyama Y: Expression of microglial response factor-1 in microglia and macrophages following cerebral ischemia in the rat. *Brain Res* 2000, 882(1-2):206-211.
29. Ng Y K, Ling E A: Microglial reaction in focal cerebral ischaemia induced by intra-carotid homologous clot injection. *Histol Histopathol* 2001, 16(1):167-174.
30. Beschorner R, Schluesener H J, Gozalan F, Meyermann R, Schwab J M: Infiltrating CD14+ monocytes and expression of CD14 by activated parenchymal microglia/macrophages contribute to the pool of CD14+ cells in ischemic brain lesions. *J Neuroimmunol* 2002, 126(1-2): 107-115.
31. Gregersen R, Lambertsen K, Finsen B: Microglia and macrophages are the major source of tumor necrosis factor in permanent middle cerebral artery occlusion in mice. *J Cereb Blood Flow Metab* 2000, 20(1):53-65.
32. Kaushal V, Schlichter L C: Mechanisms of microglia-mediated neurotoxicity in a new model of the stroke penumbra. *J Neurosci* 2008, 28(9):2221-2230.
33. Badiola N, Malagelada C, Llecha N, Hidalgo J, Comella J X, Sabria J, Rodriguez-Alvarez J: Activation of caspase-8 by tumour necrosis factor receptor 1 is necessary for caspase-3 activation and apoptosis in oxygen-glucose deprived cultured cortical cells. *Neurobiol Dis* 2009, 35(3):438-447.
34. Dziewulska D, Mossakowski M J: Cellular expression of tumor necrosis factor a and its receptors in human ischemic stroke. *Clin Neuropathol* 2003, 22(1):35-40.

35. Mayne M, Ni W, Yan H J, Xue M, Johnston J B, Del Bigio M R, Peeling J, Power C: Antisenseoligodeoxynucleotide inhibition of tumor necrosis factor-alpha expression is neuroprotective after intracerebral hemorrhage. *Stroke* 2001, 32(1):240-248.
36. Yli-Karjanmaa M, Clausen B H, Degn M, Novrup H G, Ellman D G, Toft-Jensen P, Szymkowski D E, Stensballe A, Meyer M, Brambilla R et al: Topical Administration of a Soluble TNF Inhibitor Reduces Infarct Volume After Focal Cerebral Ischemia in Mice. *Front Neurosci* 2019, 13:781.
37. Wu M H, Huang C C, Chio C C, Tsai K J, Chang C P, Lin N K, Lin M T: Inhibition of PeripheralTNF-alpha and Downregulation of Microglial Activation by Alpha-Lipoic Acid and Etanercept Protect Rat Brain Against Ischemic Stroke. *Mol Neurobiol* 2016, 53(7):4961-4971.
38. Clausen B H, Degn M, Martin N A, Couch Y, Karimi L, Ormhoj M, Mortensen M L, Gredal H B, Gardiner C, Sargent, I I et al: Systemically administered anti-TNF therapy ameliorates functional outcomes after focal cerebral ischemia. *J Neuroinflammation* 2014, 11:203.
39. Tuttolomondo A, Pecoraro R, Pinto A: Studies of selective TNF inhibitors in the treatment of brain injury from stroke and trauma: a review of the evidence to date. *Drug Des Devel Ther* 2014, 8:2221-2238.
40. Arango-Davila C A, Vera A, Londono A C, Echeverri A F, Canas F, Cardozo C F, Orozco J L, Rengifo J, Canas C A: Soluble or soluble/membrane TNF-alpha inhibitors protect the brainfrom focal ischemic injury in rats. *Int J Neurosci* 2015, 125(12):936-940.
41. Yrjanheikki J, Keinanen R, Pellikka M, Hokfelt T, Koistinaho J: Tetracyclines inhibit microglial activation and are neuroprotective in global brain ischemia. *Proc Natl Acad Sci USA* 1998, 95(26):15769-15774.
42. Yew W P, Djukic N D, Jayaseelan J S P, Walker F R, Roos K A A, Chataway T K, Muyderman H, Sims N R: Early treatment with minocycline following stroke in rats improves functional recovery and differentially modifies responses of peri-infarct microglia and astrocytes. *J Neuroinflammation* 2019, 16(1):6.
43. Ding J, Li Q Y, Wang X, Sun C H, Lu C Z, Xiao B G: Fasudil protects hippocampal neurons against hypoxia-reoxygenation injury by suppressing microglial inflammatory responses in mice. *J Neurochem* 2010, 114(6): 1619-1629.
44. Xin Q, Cheng B, Pan Y, Liu H, Yang C, Chen J, Bai B: Neuroprotective effects of apelin-13 on experimental ischemic stroke through suppression of inflammation. *Peptides* 2015, 63:55-62.
45. Lu D, Shen L, Mai H, Zang J, Liu Y, Tsang C K, Li K, Xu A: HMG-CoA Reductase Inhibitors Attenuate Neuronal Damage by Suppressing Oxygen Glucose Deprivation-Induced Activated Microglial Cells. *Neural Plast* 2019, 2019:7675496.
46. Gunther A, Kuppers-Tiedt L, Schneider P M, Kunert I, Berrouschot J, Schneider D, Rossner S: Reduced infarct volume and differential effects on glial cell activation after hyperbaric oxygen treatment in rat permanent focal cerebral ischaemia. *Eur J Neurosci* 2005, 21(11):3189-3194.
47. Hsieh C L, Cheng C Y, Tsai T H, Lin I H, Liu C H, Chiang S Y, Lin J G, Lao C J, Tang N Y: Paeonolreduced cerebral infarction involving the superoxide anion and microglia activation in ischemia-reperfusion injured rats. *J Ethnopharmacol* 2006, 106(2):208-215.
48. Lee M Y, Kuan Y H, Chen H Y, Chen T Y, Chen S T, Huang C C, Yang I P, Hsu Y S, Wu T S, Lee E J: Intravenous administration of melatonin reduces the intracerebral cellular inflammatory response following transient focal cerebral ischemia in rats. *J Pineal Res* 2007,42(3):297-309.
49. Kim H J, Rowe M, Ren M, Hong J S, Chen P S, Chuang D M: Histone deacetylase inhibitors exhibit anti-inflammatory and neuroprotective effects in a rat permanent ischemic model of stroke: multiple mechanisms of action. *J Pharmacol Exp Ther* 2007, 321(3):892-901.
50. Xuan A, Long D, Li J, Ji W, Hong L, Zhang M, Zhang W: Neuroprotective effects of valproicacid following transient global ischemia in rats. *Life Sci* 2012, 90(11-12):463-468.
51. Khan M, Elango C, Ansari M A, Singh I, Singh A K: Caffeic acid phenethyl ester reduces neurovascular inflammation and protects rat brain following transient focal cerebral ischemia. *J Neurochem* 2007, 102(2):365-377.
52. Wang S X, Guo H, Hu L M, Liu Y N, Wang Y F, Kang L Y, Gao X M: Caffeic acid ester fraction from Erigeron breviscapus inhibits microglial activation and provides neuroprotection. *Chin J Integr Med* 2012, 18(6):437-444.
53. de Bilbao F, Arsenijevic D, Moll T, Garcia-Gabay I, Vallet P, Langhans W, Giannakopoulos P: In vivo overexpression of interleukin-10 increases resistance to focal brain ischemia in mice. *J Neurochem* 2009, 110(1):12-22.
54. Wang Q, van Hoecke M, Tang X N, Lee H, Zheng Z, Swanson R A, Yenari M A: Pyruvate protects against experimental stroke via an anti-inflammatory mechanism. *Neurobiol Dis* 2009, 36(1):223-231.
55. Sharma S, Yang B, Strong R, Xi X, Brenneman M, Grotta J C, Aronowski J, Savitz S I: Bone marrow mononuclear cells protect neurons and modulate microglia in cell culture models of ischemic stroke. *J Neurosci Res* 2010, 88(13):2869-2876.
56. Franco E C, Cardoso M M, Gouveia A, Pereira A, Gomes-Leal W: Modulation of microglial activation enhances neuroprotection and functional recovery derived from bone marrow mononuclear cell transplantation after cortical ischemia. *Neurosci Res* 2012, 73(2):122-132.
57. Wei L, Fraser J L, Lu Z Y, Hu X, Yu S P: Transplantation of hypoxia preconditioned bone marrow mesenchymal stem cells enhances angiogenesis and neurogenesis after cerebralischemia in rats. *Neurobiol Dis* 2012, 46(3):635-645.
58. Ren X, Akiyoshi K, Vandenbark A A, Hurn P D, Offner H: Programmed death-1 pathway limits central nervous system inflammation and neurologic deficits in murine experimental stroke. *Stroke* 2011, 42(9):2578-2583.
59. Park J S, Shin J A, Jung J S, Hyun J W, Van Le T K, Kim D H, Park E M, Kim H S: Anti-inflammatory mechanism of compound K in activated microglia and its neuroprotective effect on experimental stroke in mice. *J Pharmacol Exp Ther* 2012, 341(1):59-67.
60. Kim S W, Jin Y, Shin J H, Kim I D, Lee H K, Park S, Han P L, Lee J K: Glycyrrhizic acid affords robust neuroprotection in the postischemic brain via anti-inflammatory effect by inhibitingHMGB1 phosphorylation and secretion. *Neurobiol Dis* 2012, 46(1):147-156.
61. Wakita H, Tomimoto H, Akiguchi I, Kimura J: Protective effect of cyclosporin A on white matter changes in the rat brain after chronic cerebral hypoperfusion. *Stroke* 1995, 26(8):1415-1422.
62. Ajmo C T, Jr., Vernon D O, Collier L, Hall A A, Garbuzova-Davis S, Willing A, Pennypacker K R: The spleen contributes to stroke-induced neurodegeneration. *J Neurosci Res* 2008, 86(10):2227-2234.

63. Krupinski J, Kaluza J, Kumar P, Kumar S, Wang J M: Role of angiogenesis in patients with cerebral ischemic stroke. *Stroke* 1994, 25(9):1794-1798.
64. Schneider U C, Schilling L, Schroeck H, Nebe C T, Vajkoczy P, Woitzik J: Granulocyte-macrophage colony-stimulating factor-induced vessel growth restores cerebral blood supply after bilateral carotid artery occlusion. *Stroke* 2007, 38(4):1320-1328.
65. Ardelt A A, Anjum N, Rajneesh K F, Kulesza P, Koehler R C: Estradiol augments peri-infarct cerebral vascular density in experimental stroke. *Exp Neurol* 2007, 206(1): 95-100.
66. Arai K, Jin G, Navaratna D, Lo E H: Brain angiogenesis in developmental and pathological processes: neurovascular injury and angiogenic recovery after stroke. *FEBS J* 2009, 276(17):4644-4652.
67. Jin Y, Barnett A, Zhang Y, Yu X, Luo Y: Poststroke Sonic Hedgehog Agonist Treatment Improves Functional Recovery by Enhancing Neurogenesis and Angiogenesis. *Stroke* 2017, 48(6):1636-1645.
68. Kanazawa M, Takahashi T, Ishikawa M, Onodera O, Shimohata T, Del Zoppo G J: Angiogenesisin the ischemic core: A potential treatment target? *J Cereb Blood Flow Metab* 2019, 39(5):753-769.
69. Marushima A, Nieminen M, Kremenetskaia I, Gianni-Barrera R, Woitzik J, von Degenfeld G, Banfi A, Vajkoczy P, Hecht N: Balanced single-vector co-delivery of VEGF/PDGF-BB improves functional collateralization in chronic cerebral ischemia. *J Cereb Blood Flow Metab* 2019:271678X18818298.
70. Iyer N V, Kotch L E, Agani F, Leung S W, Laughner E, Wenger R H, Gassmann M, Gearhart J D, Lawler A M, Yu A Y et al: Cellular and developmental control of 02 homeostasis by hypoxia-inducible factor 1 alpha. *Genes Dev* 1998, 12(2):149-162.
71. Bergeron M, Yu A Y, Solway K E, Semenza G L, Sharp F R: Induction of hypoxia-inducible factor-1 (HIF-1) and its target genes following focal ischaemia in rat brain. *Eur J Neurosci* 1999, 11(12):4159-4170.
72. Zhang Z, Yan J, Chang Y, ShiDu Yan S, Shi H: Hypoxia inducible factor-1 as a target for neurodegenerative diseases. *Curr Med Chem* 2011, 18(28):4335-4343.
73. Liu B N, Han B X, Liu F: Neuroprotective effect of pAkt and HIF-1 alpha on ischemia rats. *Asian Pac J Trop Med* 2014, 7(3):221-225.
74. Huang T, Huang W, Zhang Z, Yu L, Xie C, Zhu D, Peng Z, Chen J: Hypoxia-inducible factor-1alpha upregulation in microglia following hypoxia protects against ischemia-induced cerebral infarction. *Neuroreport* 2014, 25(14): 1122-1128.
75. Kumar H, Choi D K: Hypoxia Inducible Factor Pathway and Physiological Adaptation: A Cell Survival Pathway? *Mediators Inflamm* 2015, 2015:584758.
76. Ceradini D J, Kulkarni A R, Callaghan M J, Tepper O M, Bastidas N, Kleinman M E, Capla J M, Galiano R D, Levine J P, Gurtner G C: Progenitor cell trafficking is regulated by hypoxic gradients through HIF-1 induction of SDF-1. *Nat Med* 2004, 10(8):858-864.
77. Ceradini D J, Gurtner G C: Homing to hypoxia: HIF-1 as a mediator of progenitor cell recruitment to injured tissue. *Trends Cardiovasc Med* 2005, 15(2):57-63.
78. Tabatabai G, Frank B, Mohle R, Weller M, Wick W: Irradiation and hypoxia promote homing of haematopoietic progenitor cells towards gliomas by TGF-beta-dependent HIF-1alpha-mediated induction of CXCL12. *Brain* 2006, 129(Pt 9):2426-2435.
79. Chang Y C, Shyu W C, Lin S Z, Li H: Regenerative therapy for stroke. *Cell Transplant* 2007, 16(2):171-181.
80. Hoenig M R, Bianchi C, Sellke F W: Hypoxia inducible factor-1 alpha, endothelial progenitor cells, monocytes, cardiovascular risk, wound healing, cobalt and hydralazine: a unifying hypothesis. *Curr Drug Targets* 2008, 9(5):422-435.
81. Marti H J, Bernaudin M, Bellail A, Schoch H, Euler M, Petit E, Risau W: Hypoxia-induced vascular endothelial growth factor expression precedes neovascularization after cerebralischemia. *Am J Pathol* 2000, 156(3):965-976.
82. Harms K M, Li L, Cunningham L A: Murine neural stem/progenitor cells protect neurons against ischemia by HIF-1alpha-regulated VEGF signaling. *PLoS One* 2010, 5(3):e9767.
83. Cunningham L A, Candelario K, Li L: Roles for HIF-1alpha in neural stem cell function and the regenerative response to stroke. *Behav Brain Res* 2012, 227(2):410-417.
84. Lai T W, Lin S Z, Lee H T, Fan J R, Hsu Y H, Wang H J, Yu Y L, Shyu W C: HIF-1alpha binding to the Epac1 promoter recruits hematopoietic stem cells to the ischemic brain following stroke. *J Mol Cell Biol* 2012, 4(3):184-187.
85. Hu Q, Liang X, Chen D, Chen Y, Doycheva D, Tang J, Tang J, Zhang J H: Delayed hyperbaricoxygen therapy promotes neurogenesis through reactive oxygen species/hypoxia-inducible factor-1alpha/beta-catenin pathway in middle cerebral artery occlusion rats. *Stroke* 2014, 45(6): 1807-1814.
86. Khan M, Dhammu T S, Matsuda F, Baarine M, Dhindsa T S, Singh I, Singh A K: Promotingendothelial function by S-nitrosoglutathione through the HIF-1alpha/VEGF pathway stimulates neurorepair and functional recovery following experimental stroke in rats. *Drug Des Devel Ther* 2015, 9:2233-2247.
87. Badawi Y, Ramamoorthy P, Shi H: Hypoxia-inducible factor 1 protects hypoxic astrocytes against glutamate toxicity. *ASN Neuro* 2012, 4(4):231-241.
88. Chen J, Li Y, Chopp M: Intracerebral transplantation of bone marrow with BDNF after MCAo in rat. *Neuropharmacology* 2000, 39(5):711-716.
89. Li Y, Chen J, Chopp M: Adult bone marrow transplantation after stroke in adult rats. *Cell Transplant* 2001, 10(1):31-40.
90. Li Y, Chen J, Wang L, Lu M, Chopp M: Treatment of stroke in rat with intracarotid administration of marrow stromal cells. *Neurology* 2001, 56(12):1666-1672.
91. Zhang Z G, Zhang L, Jiang Q, Chopp M: Bone marrow-derived endothelial progenitor cells participate in cerebral neovascularization after focal cerebral ischemia in the adult mouse. *Circ Res* 2002, 90(3):284-288.
92. Zhao L R, Duan W M, Reyes M, Keene C D, Verfaillie C M, Low W C: Human bone marrow stem cells exhibit neural phenotypes and ameliorate neurological deficits after grafting intothe ischemic brain of rats. *Exp Neurol* 2002, 174(1):11-20.
93. Hess D C, Hill W D, Martin-Studdard A, Carroll J, Brailer J, Carothers J: Bone marrow as a source of endothelial cells and NeuN-expressing cells After stroke. *Stroke* 2002, 33(5):1362-1368.
94. Willing A E, Vendrame M, Mallery J, Cassady C J, Davis C D, Sanchez-Ramos J, Sanberg P R: Mobilized peripheral blood cells administered intravenously produce functional recovery instroke. *Cell Transplant* 2003, 12(4):449-454.

95. Hill W D, Hess D C, Martin-Studdard A, Carothers J J, Zheng J, Hale D, Maeda M, Fagan S C, Carroll J E, Conway S J: SDF-1 (CXCL12) is upregulated in the ischemic penumbra following stroke: association with bone marrow cell homing to injury. *J Neuropathol Exp Neurol* 2004,63(1):84-96.
96. Shyu W C, Lin S Z, Yang H I, Tzeng Y S, Pang C Y, Yen P S, Li H: Functional recovery of strokerats induced by granulocyte colony-stimulating factor-stimulated stem cells. *Circulation* 2004, 110(13):1847-1854.
97. Shen L H, Li Y, Chen J, Zhang J, Vanguri P, Borneman J, Chopp M: Intracarotid transplantation of bone marrow stromal cells increases axon-myelin remodeling after-stroke. *Neuroscience* 2006, 137(2):393-399.
98. Baker A H, Sica V, Work L M, Williams-Ignarro S, de Nigris F, Lerman L O, Casamassimi A, Lanza A, Schiano C, Rienzo M et al: Brain protection using autologous bone marrow cell, metalloproteinase inhibitors, and metabolic treatment in cerebral ischemia. *Proc Natl Acad Sci USA* 2007, 104(9):3597-3602.
99. Wu J, Sun Z, Sun H S, Wu J, Weisel R D, Keating A, Li Z H, Feng Z P, Li R K: Intravenously Administered Bone Marrow Cells Migrate to Damaged Brain Tissue and Improve NeuralFunction in Ischemic Rats. *Cell Transplant* 2007, 16(10):993-1005.
100. Chen J R, Cheng G Y, Sheu C C, Tseng G F, Wang T J, Huang Y S: Transplanted bone marrow stromal cells migrate, differentiate and improve motor function in rats with experimentally induced cerebral stroke. *J Anat* 2008, 213(3):249-258.
101. Pavlichenko N, Sokolova I, Vijde S, Shvedova E, Alexandrov G, Krouglyakov P, Fedotova O, Gilerovich E G, Polyntsev D G, Otellin V A: Mesenchymal stem cells transplantation could be beneficial for treatment of experimental ischemic stroke in rats. *Brain Res* 2008, 1233: 203-213.
102. Omori Y, Honmou O, Harada K, Suzuki J, Houkin K, Kocsis J D: Optimization of a therapeutic protocol for intravenous injection of human mesenchymal stem cells after cerebral is chemiain adult rats. *Brain Res* 2008, 1236:30-38.
103. Chen Z Z, Jiang X D, Zhang L L, Shang J H, Du M X, Xu G, Xu R X: Beneficial effect of autologous transplantation of bone marrow stromal cells and endothelial progenitor cells oncerebral ischemia in rabbits. *Neurosci Lett* 2008, 445(1):36-41.
104. Keimpema E, Fokkens M R, Nagy Z, Agoston V, Luiten P G, Nyakas C, Boddeke H W, Copray J C: Early transient presence of implanted bone marrow stem cells reduces lesion size after cerebral ischaemia in adult rats. *Neuropathol Appl Neurobiol* 2009, 35(1):89-102.
105. Yasuhara T, Matsukawa N, Hara K, Maki M, Ali M M, Yu S J, Bae E, Yu G, Xu L, McGrogan M et al: Notch-induced rat and human bone marrow stromal cell grafts reduce ischemic cell loss and ameliorate behavioral deficits in chronic stroke animals. *Stem Cells Dev* 2009, 18(10):1501-1514.
106. Deng Y B, Ye W B, Hu Z Z, Yan Y, Wang Y, Takon B F, Zhou G Q, Zhou Y F: Intravenously administered BMSCs reduce neuronal apoptosis and promote neuronal proliferation through the release of VEGF after stroke in rats. *Neurol Res* 2010, 32(2):148-156.
107. Liu N, Chen R, Du H, Wang J, Zhang Y, Wen J: Expression of IL-10 and TNF-alpha in rats with cerebral infarction after transplantation with mesenchymal stem cells. *Cell Mol Immunol* 2009, 6(3):207-213.
108. Yang M, Wei X, Li J, Heine L A, Rosenwasser R, Iacovitti L: Changes in host blood factors and brain glia accompanying the functional recovery after systemic administration of bonemarrow stem cells in ischemic stroke rats. *Cell Transplant* 2010, 19(9):1073-1084.
109. Shen L H, Li Y, Chopp M: Astrocytic endogenous glial cell derived neurotrophic factor production is enhanced by bone marrow stromal cell transplantation in the ischemic boundary zone after stroke in adult rats. *Glia* 2010, 58(9):1074-1081.
110. Yilmaz G, Alexander J S, Erkuran Yilmaz C, Granger D N: Induction of neuro-protective/regenerative genes in stem cells infiltrating post-ischemic brain tissue. *Exp Transl Stroke Med* 2010, 2(1):11.
111. Felfly H, Muotri A, Yao H, Haddad G G: Hematopoietic stem cell transplantation protects mice from lethal stroke. *Exp Neurol* 2010, 225(2):284-293.
112. Zhang X M, Du F, Yang D, Yu C J, Huang X N, Liu W, Fu J: Transplanted bone marrow stem cells relocate to infarct penumbra and co-express endogenous proliferative and immatureneuronal markers in a mouse model of ischemic cerebral stroke. *BMC Neurosci* 2010, 11:138.
113. Lowrance S A, Fink K D, Crane A, Matyas J, Dey N D, Matchynski J J, Thibo T, Reinke T, Kippe J, Hoffman C et al: Bone-marrow-derived mesenchymal stem cells attenuate cognitive deficits in an endothelin-1 rat model of stroke. *Restor Neurol Neurosci* 2015, 33(4):579-588.
114. Yang B, Migliati E, Parsha K, Schaar K, Xi X, Aronowski J, Savitz S I: Intra-arterial delivery is not superior to intravenous delivery of autologous bone marrow mononuclear cells in acute ischemic stroke. *Stroke* 2013, 44(12):3463-3472.
115. Sharma A, Sane H, Nagrajan A, Gokulchandran N, Badhe P, Paranjape A, Biju H: Autologous bone marrow mononuclear cells in ischemic cerebrovascular accident paves way for neurorestoration: a case report. *Case Rep Med* 2014, 2014:530239.
116. Li N, Wang P, Ma X L, Wang J, Zhao L J, Du L, Wang L Y, Wang X R, Liu K D: Effect of bone marrow stromal cell transplantation on neurologic function and expression of VEGF in ratswith focal cerebral ischemia. *Mol Med Rep* 2014, 10(5):2299-2305.
117. Du S, Guan J, Mao G, Liu Y, Ma S, Bao X, Gao J, Feng M, Li G, Ma W et al: Intra-arterial delivery of human bone marrow mesenchymal stem cells is a safe and effective way to treat cerebral ischemia in rats. *Cell Transplant* 2014, 23 Suppl 1:573-82.
118. Fukuda Y, Horie N, Satoh K, Yamaguchi S, Morofuji Y, Hiu T, Izumo T, Hayashi K, Nishida N, Nagata I: Intra-arterial transplantation of low-dose stem cells provides functional recovery without adverse effects after stroke. *Cell Mol Neurobiol* 2015, 35(3):399-406.
119. Xu Y, Du S, Yu X, Han X, Hou J, Guo H: Human bone marrow mesenchymal stem cell transplantation attenuates axonal injury in stroke rats. *Neural Regen Res* 2014, 9(23):2053-2058.
120. Moniche F, Escudero I, Zapata-Arriaza E, Usero-Ruiz M, Prieto-Leon M, de la Torre J, Gamero M A, Tamayo J A, Ochoa-Sepulveda J J, Maestre J et al: Intra-arterial bone marrow mononuclear cells (B M-MNCs) transplantation in acute ischemic stroke (*IBIS* trial): protocol of a phase II, randomized, dose-finding, controlled multi-center trial. *Int J Stroke* 2015, 10(7):1149-1152.
121. Yang Z, Cai X, Xu A, Xu F, Liang Q: Bone marrow stromal cell transplantation through tail vein injection promotes angiogenesis and vascular endothelial growth factor expression in cerebral infarct area in rats. *Cytotherapy* 2015, 17(9):1200-1212.
122. Lapi D, Vagnani S, Sapio D, Mastantuono T, Boscia F, Pignataro G, Penna C, Pagliaro P, Colantuoni A: Effects of bone marrow mesenchymal stem cells (B M-MSCs) on rat pial microvascular remodeling after transient middle cerebral artery occlusion. *Front Cell Neurosci* 2015, 9:329.
123. Lv W, Li W Y, Xu X Y, Jiang H, Bang O Y: Bone marrow mesenchymal stem cells transplantation promotes the release of endogenous erythropoietin after ischemic stroke. *Neural Regen Res* 2015, 10(8):1265-1270.
124. He Q Q, He X, Wang Y P, Zou Y, Xia Q J, Xiong L L, Luo C Z, Hu X S, Liu J, Wang T H: Transplantation of bone marrow-derived mesenchymal stem cells (BMSCs) improves brain ischemia-induced pulmonary injury in rats associated to TNF-alpha expression. *Behav Brain Funct* 2016, 12(1):9.
125. Hu J, Liu B, Zhao Q, Jin P, Hua F, Zhang Z, Liu Y, Zan K, Cui G, Ye X: Bone marrow stromalcells inhibits HMGB1-mediated inflammation after stroke in type 2 diabetic rats. *Neuroscience* 2016, 324:11-19.
126. Yang B, Parsha K, Schaar K, Xi X, Aronowski J, Savitz S I: Various Cell Populations Within the Mononuclear Fraction of Bone Marrow Contribute to the Beneficial Effects of Autologous Bone Marrow Cell Therapy in a Rodent Stroke Model. *Transl Stroke Res* 2016,7(4):322-330.
127. Li Y, Chen C H, Yin Y, Mao W W, Hua X M, Cheng J: Neuroprotection by intravenous transplantation of bone marrow mononuclear cells from 5-fluorouracil pre-treated rats in amodel of ischemic stroke. *Neurol Res* 2016, 38(10):921-928.
128. Sasaki Y, Sasaki M, Kataoka-Sasaki Y, Nakazaki M, Nagahama H, Suzuki J, Tateyama D, Oka S, Namioka T, Namioka A et al: Synergic Effects of Rehabilitation and Intravenous Infusion of Mesenchymal Stem Cells After Stroke in Rats. *Phys Ther* 2016, 96(11):1791-1798.
129. Ghali A A, Yousef M K, Ragab O A, ElZamarany E A: Intra-arterial Infusion of Autologous Bone Marrow Mononuclear Stem Cells in Subacute Ischemic Stroke Patients. *Front Neurol* 2016, 7:228.
130. Garbuzova-Davis S, Haller E, Lin R, Borlongan C V: Intravenously Transplanted Human Bone Marrow Endothelial Progenitor Cells Engraft Within Brain Capillaries, Preserve Mitochondrial Morphology, and Display Pinocytotic Activity Toward Blood-Brain BarrierRepair in Ischemic Stroke Rats. *Stem Cells* 2017, 35(5):1246-1258.
131. Nakamura H, Sasaki Y, Sasaki M, Kataoka-Sasaki Y, Oka S, Nakazaki M, Namioka T, NamiokaA, Onodera R, Suzuki J et al: Elevated brain derived neurotrophic factor levels in plasma reflect in vivo functional viability of infused mesenchymal stem cells for stroke in rats. *J Neurosurg Sci* 2019, 63(1):42-49.
132. Yang B, Hamilton J A, Valenzuela K S, Bogaerts A, Xi X, Aronowski J, Mays R W, Savitz S I: Multipotent Adult Progenitor Cells Enhance Recovery After Stroke by Modulating the Immune Response from the Spleen. *Stem Cells* 2017, 35(5):1290-1302.
133. Sammali E, Alia C, Vegliante G, Colombo V, Giordano N, Pischiutta F, Boncoraglio G B, Barilani M, Lazzari L, Caleo M et al: Intravenous infusion of human bone marrow mesenchymal stromal cells promotes functional recovery and neuroplasticity after ischemic stroke in mice. *Sci Rep* 2017, 7(1):6962.
134. Vibhuti, Khan R, Sharma A, Jain S, Mohanty S, Prasad K: Intra-arterial transplantation of human bone marrow mesenchymal stem cells (hBMMSCs) improves behavioral deficits and alters gene expression in rodent stroke model. *J Neurochem* 2017, 143(6):722-735.
135. Yu X, Wu H, Zhao Y, Guo Y, Chen Y, Dong P, Mu Q, Wang X, Wang X: Bone marrow mesenchymal stromal cells alleviate brain white matter injury via the enhanced proliferation of oligodendrocyte progenitor cells in focal cerebral ischemic rats. *Brain Res* 2018, 1680:127-136.
136. Bhatia V, Gupta V, Khurana D, Sharma R R, Khandelwal N: Randomized Assessment of the Safety and Efficacy of Intra-Arterial Infusion of Autologous Stem Cells in Subacute Ischemic Stroke. *AJNR Am J Neuroradiol* 2018, 39(5):899-904.
137. Chau M J, Deveau T C, Gu X, Kim Y S, Xu Y, Yu S P, Wei L: Delayed and repeated intranasal delivery of bone marrow stromal cells increases regeneration and functional recovery after ischemic stroke in mice. *BMC Neurosci* 2018, 19(1):20.
138. Li X, Huang M, Zhao R, Zhao C, Liu Y, Zou H, Chen L, Guan Y, Zhang Y A: Intravenously Delivered Allogeneic Mesenchymal Stem Cells Bidirectionally Regulate Inflammation and Induce Neurotrophic Effects in Distal Middle Cerebral Artery Occlusion Rats Within the First 7 Days After Stroke. *Cell Physiol Biochem* 2018, 46(5):1951-1970.
139. Bi M, Wang J, Zhang Y, Li L, Wang L, Yao R, Duan S, Tong S, Li J: Bone mesenchymal stemcells transplantation combined with mild hypothermia improves the prognosis of cerebral ischemia in rats. *PLoS One* 2018, 13(8):e0197405.
140. Ito Y, Tsurushima H, Sato M, Ito A, Oyane A, Sogo Y, Matsumura A: Angiogenesis therapy forbrain infarction using a slow-releasing drug delivery system for fibroblast growth factor 2. *Biochem Biophys Res Commun* 2013, 432(1):182-187.
141. Kawada H, Takizawa S, Takanashi T, Morita Y, Fujita J, Fukuda K, Takagi S, Okano H, Ando K, Hotta T: Administration of hematopoietic cytokines in the subacute phase after cerebral infarction is effective for functional recovery facilitating proliferation of intrinsic neural stem/progenitor cells and transition of bone marrow-derived neuronal cells. *Circulation* 2006, 113(5):701-710.
142. Shichinohe H, Kuroda S, Yano S, Ohnishi T, Tamagami H, Hida K, Iwasaki Y: Improved expression of gamma-aminobutyric acid receptor in mice with cerebral infarct and transplanted bone marrow stromal cells: an autoradiographic and histologic analysis. *J Nucl Med* 2006, 47(3):486-491.
143. Yoo S W, Kim S S, Lee S Y, Lee H S, Kim H S, Lee Y D, Suh-Kim H: Mesenchymal stem cells promote proliferation of endogenous neural stem cells and survival of newborn cells in a ratstroke model. *Exp Mol Med* 2008, 40(4):387-397.
144. Thored P, Heldmann U, Gomes-Leal W, Gisler R, Darsalia V, Taneera J, Nygren J M, Jacobsen S E, Ekdahl C T, Kokaia Z et al: Long-term accumulation of microglia with proneurogenic phenotype concomitant with persistent neurogenesis in adult subventricular zone after stroke. *Glia* 2009, 57(8):835-849.
145. Chen Z, Hu Q, Xie Q, Wu S, Pang Q, Liu M, Zhao Y, Tu F, Liu C, Chen X: Effects of Treadmill Exercise on Motor and Cognitive Function Recovery of MCAO Mice Through the Caveolin-1/VEGF Signaling Pathway in Ischemic Penumbra. *Neurochem Res* 2019, 44(4):930-946.

146. Zhou J, Liu T, Guo H, Cui H, Li P, Feng D, Hu E, Huang Q, Yang A, Zhou J et al: Lactate potentiates angiogenesis and neurogenesis in experimental intracerebral hemorrhage. *Exp Mol Med* 2018, 50(7):78.
147. Chen D, Wei L, Liu Z R, Yang J J, Gu X, Wei Z Z, Liu L P, Yu S P: Pyruvate Kinase M2 Increases Angiogenesis, Neurogenesis, and Functional Recovery Mediated by Upregulationof STAT3 and Focal Adhesion Kinase Activities After Ischemic Stroke in Adult Mice. *Neurotherapeutics* 2018, 15(3):770-784.
148. Xiao W, Zhan Q, Ye F, Tang X, Li J, Dong H, Sha W, Zhang X: Elevated serum vascularendothelial growth factor in treatment-resistant schizophrenia treated with electroconvulsive therapy: Positive association with therapeutic effects. *World J Biol Psychiatry* 2019, 20(2):150-158.
149. Li C, Zhang B, Zhu Y, Li Y, Liu P, Gao B, Tian S, Du L, Bai Y: Post-stroke Constraint-induced Movement Therapy Increases Functional Recovery, Angiogenesis, and Neurogenesis with Enhanced Expression of HIF-1alpha and VEGF. *Curr Neurovasc Res* 2017, 14(4):368-377.
150. Doeppner T R, Traut V, Heidenreich A, Kaltwasser B, Bosche B, Bahr M, Hermann D M: Conditioned Medium Derived from Neural Progenitor Cells Induces Long-term Post-ischemic Neuroprotection, Sustained Neurological Recovery, Neurogenesis, and Angiogenesis. *Mol Neurobiol* 2017, 54(2):1531-1540.
151. Park H W, Moon H E, Kim H S, Paek S L, Kim Y, Chang J W, Yang Y S, Kim K, Oh W, Hwang J H et al: Human umbilical cord blood-derived mesenchymal stem cells improve functional recovery through thrombospondin1, pantraxin3, and vascular endothelial growth factor in the ischemic rat brain. *J Neurosci Res* 2015, 93(12):1814-1825.
152. Ruan L, Wang B, ZhuGe Q, Jin K: Coupling of neurogenesis and angiogenesis after ischemic stroke. *Brain Res* 2015, 1623:166-173.
153. Carmeliet P, Ruiz de Almodovar C: VEGF ligands and receptors: implications in neurodevelopment and neurodegeneration. *Cell Mol Life Sci* 2013, 70(10):1763-1778.
154. Thomas J L, Eichmann A: The power of VEGF (vascular endothelial growth factor) family molecules. *Cell Mol Life Sci* 2013, 70(10):1673-1674.
155. Calvo C F, Fontaine R H, Soueid J, Tammela T, Makinen T, Alfaro-Cervello C, Bonnaud F, Miguez A, Benhaim L, Xu Y et al: Vascular endothelial growth factor receptor 3 directly regulates murine neurogenesis. *Genes Dev* 2011, 25(8):831-844.
156. Licht T, Goshen I, Avital A, Kreisel T, Zubedat S, Eavri R, Segal M, Yirmiya R, Keshet E: Reversible modulations of neuronal plasticity by VEGF. *Proc Natl Acad Sci USA* 2011, 108(12):5081-5086.
157. Sun J, Sha B, Zhou W, Yang Y: VEGF-mediated angiogenesis stimulates neural stem cell proliferation and differentiation in the premature brain. *Biochem Biophys Res Commun* 2010, 394(1):146-152.
158. Hansen T M, Moss A J, Brindle N P: Vascular endothelial growth factor and angiopoietins in neurovascular regeneration and protection following stroke. *Curr Neurovasc Res* 2008, 5(4):236-245.
159. Plaschke K, Staub J, Ernst E, Marti H H: VEGF overexpression improves mice cognitive abilities after unilateral common carotid artery occlusion. *Exp Neurol* 2008, 214(2):285-292.
160. Wang L, Chopp M, Gregg S R, Zhang R L, Teng H, Jiang A, Feng Y, Zhang Z G: Neural progenitor cells treated with EPO induce angiogenesis through the production of VEGF. *J Cereb Blood Flow Metab* 2008, 28(7):1361-1368.
161. Wang Y Q, Guo X, Qiu M H, Feng X Y, Sun F Y: VEGF overexpression enhances striatal neurogenesis in brain of adult rat after a transient middle cerebral artery occlusion. *J Neurosci Res* 2007, 85(1):73-82.
162. Sun Y, Jin K, Xie L, Childs J, Mao X O, Logvinova A, Greenberg D A: VEGF-induced neuroprotection, neurogenesis, and angiogenesis after focal cerebral ischemia. *J Clin Invest* 2003, 111(12):1843-1851.
163. Jin K, Zhu Y, Sun Y, Mao X O, Xie L, Greenberg D A: Vascular endothelial growth factor (VEGF) stimulates neurogenesis in vitro and in vivo. *Proc Natl Acad Sci USA* 2002, 99(18):11946-11950.
164. Siqueira M, Francis D, Gisbert D, Gomes FCA, Stipursky J: Radial Glia Cells Control Angiogenesis in the Developing Cerebral Cortex Through TGF-beta1 Signaling. *Mol Neurobiol* 2018, 55(5):3660-3675.
165. Meng Z, Li M, He Q, Jiang S, Zhang X, Xiao J, Bai Y: Ectopic expression of human angiopoietin-1 promotes functional recovery and neurogenesis after focal cerebral ischemia. *Neuroscience* 2014, 267:135-146.
166. Bai Y, Cui M, Meng Z, Shen L, He Q, Zhang X, Chen F, Xiao J: Ectopic expression of angiopoietin-1 promotes neuronal differentiation in neural progenitor cells through the Aktpathway. *Biochem Biophys Res Commun* 2009, 378(2):296-301.
167. Pringle N P, Mudhar H S, Collarini E J, Richardson W D: PDGF receptors in the rat CNS: during late neurogenesis, PDGF alpha-receptor expression appears to be restricted to glialcells of the oligodendrocyte lineage. *Development* 1992, 115(2):535-551.
168. Jin K, Galvan V, Xie L, Mao X O, Gorostiza O F, Bredesen D E, Greenberg D A: Enhanced neurogenesis in Alzheimer's disease transgenic (PDGF-APPSw, Ind) mice. *Proc Natl Acad Sci USA* 2004, 101(36):13363-13367.
169. Mohapel P, Frielingsdorf H, Haggblad J, Zachrisson O, Brundin P: Platelet-derived growth factor (PDGF-BB) and brain-derived neurotrophic factor (BDNF) induce striatal neurogenesis in adult rats with 6-hydroxydopamine lesions. *Neuroscience* 2005, 132(3):767-776.
170. Jackson E L, Garcia-Verdugo J M, Gil-Perotin S, Roy M, Quinones-Hinojosa A, VandenBerg S, Alvarez-Buylla A: PDGFR alpha-positive B cells are neural stem cells in the adult SVZ that form glioma-like growths in response to increased PDGF signaling. *Neuron* 2006, 51(2):187-199.
171. Funa K, Sasahara M: The roles of PDGF in development and during neurogenesis in the normal and diseased nervous system. *J Neuroimmune Pharmacol* 2014, 9(2):168-181.
172. Moore L, Bain J M, Loh J M, Levison S W: PDGF-responsive progenitors persist in the subventricular zone across the lifespan. *ASN Neuro* 2014, 6(2).
173. Sil S, Periyasamy P, Thangaraj A, Chivero E T, Buch S: PDGF/PDGFR axis in the neuralsystems. *Mol Aspects Med* 2018, 62:63-74.
174. Chen J, Zacharek A, Zhang C, Jiang H, Li Y, Roberts C, Lu M, Kapke A, Chopp M: Endothelialnitric oxide synthase regulates brain-derived neurotrophic factor expression and neurogenesis after stroke in mice. *J Neurosci* 2005, 25(9):2366-2375.
175. Madri J A: Modeling the neurovascular niche: implications for recovery from CNS injury. *J Physiol Pharmacol* 2009, 60 Suppl 4:95-104.

176. Pikula A, Beiser A S, Chen T C, Preis S R, Vorgias D, DeCarli C, Au R, Kelly-Hayes M, Kase C S, Wolf P A et al: Serum brain-derived neurotrophic factor and vascular endothelial growth factor levels are associated with risk of stroke and vascular brain injury: Framingham Study. *Stroke* 2013, 44(10):2768-2775.

177. Lin C Y, Hung S Y, Chen H T, Tsou H K, Fong Y C, Wang S W, Tang C H: Brain-derived neurotrophic factor increases vascular endothelial growth factor expression and enhancesangiogenesis in human chondrosarcoma cells. *Biochem Pharmacol* 2014, 91(4):522-533.

178. Lu L, Bai X, Cao Y, Luo H, Yang X, Kang L, Shi M J, Fan W, Zhao B Q: Growth Differentiation Factor 11 Promotes Neurovascular Recovery After Stroke in Mice. *Front Cell Neurosci* 2018, 12:205.

179. Schafer M J, LeBrasseur N K: The influence of GDF11 on brain fate and function. *Geroscience* 2019, 41(1):1-11.

180. Toh H, Daniels E, Bateman A: Methods to Investigate the Roles of Progranulin in Angiogenesis Using In Vitro Strategies and Transgenic Mouse Models. *Methods Mol Biol* 2018, 1806:329-360.

The invention claimed is:

1. A method of protecting from damage and/or regenerating a neurological tissue, comprising administration of:
   (a) pterostilbene, and/or blueberry, and/or an extract thereof;
   (b) green tea and/or an extract thereof;
   (c) *Nigella sativa* and/or an extract thereof; and
   (d) broccoli and/or an extract thereof.

2. The method of claim 1, wherein said neurological protection is inhibition of neuronal apoptosis.

3. The method of claim 1, wherein said neurological protection is inhibition of neuronal dysfunction.

4. The method of claim 1, wherein said neurological protection is inhibition of neuronal excitotoxicity.

5. The method of claim 1, wherein said neurological protection is inhibition of neuronal oxidative stress.

6. The method of claim 1, wherein said neurological protection is upregulation of Bcl-2.

7. The method of claim 1, wherein said neurological protection is downregulation of Fas ligand (FasL).

8. The method of claim 1, wherein said neurological protection is downregulation of Fas.

9. The method of claim 1, wherein said regeneration of said neurological tissue comprises stimulation of axonal re-connections.

10. The method of claim 1, wherein said regeneration of said neurological tissue comprises stimulation of proliferation of neural progenitor cells.

11. The method of claim 10, wherein said neural progenitor cells are endogenous.

12. The method of claim 11, wherein said endogenous neural progenitor cells are originating from the subventricular.

13. The method of claim 11, wherein said endogenous neural progenitor cells are originating from the dendate gyrus of the hippocampus.

14. The method of claim 10, wherein said neural progenitor cells are exogenous.

15. The method of claim 1, wherein said green tea extract is epigallocatechin-3-gallate or an analogue thereof.

16. The method of claim 1, wherein said blueberry extract is pterostilebene or an analogue thereof.

17. The method of claim 1, wherein said *Nigella sativa* extract is thymoquinone or an analogue thereof.

18. The method of claim 1, wherein said broccoli extract is sulforaphane or an analogue thereof.

19. The method of claim 1, wherein said neurological damage is COVID-19 associated.

* * * * *